US008772476B2

(12) United States Patent
Levy et al.

(10) Patent No.: US 8,772,476 B2
(45) Date of Patent: Jul. 8, 2014

(54) GAS AND LIQUID PHASE CATALYTIC BECKMANN REARRANGEMENT OF OXIMES TO PRODUCE LACTAMS

(71) Applicants: Honeywell International Inc., Morristown, NJ (US); University of Southampton, Southampton (GB)

(72) Inventors: Alan B. Levy, Randolph, NJ (US); Robert Raja, Eastleigh (GB); Matthew E. Potter, Southampton (GB)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/658,495

(22) Filed: Oct. 23, 2012

(65) Prior Publication Data

US 2013/0109851 A1    May 2, 2013

Related U.S. Application Data

(60) Provisional application No. 61/628,419, filed on Oct. 28, 2011.

(51) Int. Cl.
*C07D 201/04* (2006.01)
*C07D 223/10* (2006.01)

(52) U.S. Cl.
USPC .......................................... 540/535; 540/536

(58) Field of Classification Search
USPC .................................................. 540/535, 536
See application file for complete search history.

(56) References Cited

U.S. PATENT DOCUMENTS

| | | | |
|---|---|---|---|
| 3,503,958 A | 3/1970 | Landis | |
| 4,440,871 A | 4/1984 | Lok et al. | |
| 4,859,785 A | 8/1989 | Bellussi et al. | |
| 4,873,325 A | 10/1989 | Olson | |
| 5,242,676 A | 9/1993 | Apelian et al. | |
| 5,292,880 A | 3/1994 | Apelian et al. | |
| 5,304,643 A | 4/1994 | Kajikuri et al. | |
| 5,312,915 A | 5/1994 | Yashima et al. | |
| 5,338,861 A | 8/1994 | Botta et al. | |
| 6,303,099 B1 | 10/2001 | Ichihashi et al. | |
| 6,531,595 B2 | 3/2003 | Holderich et al. | |
| 6,645,899 B1 | 11/2003 | Palmery et al. | |
| 6,734,323 B2 | 5/2004 | Botti et al. | |
| 6,838,406 B2 | 1/2005 | Balducci et al. | |
| 6,946,553 B2 | 9/2005 | Sugita et al. | |
| 6,989,444 B2 | 1/2006 | Sultana et al. | |
| 7,060,645 B2 | 6/2006 | Hoshino et al. | |
| 7,214,637 B2 | 5/2007 | Balducci et al. | |
| 7,547,778 B2 | 6/2009 | Balducci et al. | |
| 8,212,028 B2 | 7/2012 | Okubo et al. | |
| 2007/0112189 A1 | 5/2007 | Ikeda et al. | |
| 2010/0179317 A1 | 7/2010 | Raja | |
| 2011/0257390 A1 | 10/2011 | Raja et al. | |

FOREIGN PATENT DOCUMENTS

| | | |
|---|---|---|
| CN | 1322927 | 3/2005 |
| CN | 102050464 | 5/2011 |
| CN | 102188989 | 9/2011 |
| CN | 102432032 | 9/2011 |
| CN | 102627286 | 1/2012 |
| DE | 1545789 | 2/1969 |
| EP | 1193251 A3 | 4/2002 |
| JP | 9291074 | 11/1997 |
| JP | 2001072657 A | 3/2001 |
| JP | 2001072658 A | 3/2001 |
| JP | 3969078 | 6/2003 |
| JP | 2012066977 | 4/2012 |
| WO | WO 2010/063276 | 6/2010 |

OTHER PUBLICATIONS

T.D. Consesa, et al., Novel Mesoporous Silicoaluminophosphates as Highly Active and Selective Materials in the Beckmann rearrangement of Cyclohexanone and Cyclodedecanone Oximes, Journal of Catalysts 252 (2007), p. 1-10.
Edith M. Flanigen, et al., "Aluminophosphate Molecular Sieves and the Periodic Table," Pure & Appl. Chem., vol. 58, No. 10, pp. 1351-1358, 1986.
Edith M. Flanigen, et al., Zeolites in Industrial Separation and Catalysts, Chapter 1, Introduction, p. 1-26, 2010.
N. Jappar, Y. Tanaka, S. Nakata, and T. Tatsumi, "Synthesis and Characterization of a New Titanium Silicoaluminophospate: TAPSO-37," Microporous and Mesoporous Materials, vol. 23, Issues 3-4, Aug. 1998, pp. 169-178.
Christian Baerlocher, et al., *Atlas of Zeolite Framework Types*, 6th ed., Amsterdam (2007), pp. 140-141.
D. Dubois, et al., "Conversion of methanol to olefins over cobalt-, manganese- and nickel-incorporated SAPO-34 molecular sieves", *Fuel Process. Technol*. 2003, 83, 203.
P. Meriaudeau, et al., "SAPO-11, SAPO-31, and SAPO-41 Molecular Sieves: Synthesis, Characterization, and Catalytic Properties in *n*-Octane Hydroisomerization", *Journal of catalysis*, 1997, 169, 55-66.
PCT ISR & Written Opinion issued in PCT/US2012/061876 dated Mar. 18, 2013.

*Primary Examiner* — Bruck Kifle
(74) *Attorney, Agent, or Firm* — Faegre Baker Daniels LLP

(57) ABSTRACT

Methods for producing lactams from oximes by performing a Beckmann rearrangement using a silicoaluminophosphate catalyst are provided. These catalysts may be used in gas phase or liquid phase reactions to convert oximes into lactams. High conversion of oxime and high selectivity for the desired lactams are produced using the disclosed methods, including high conversion and selectivity for ε-caprolactam produced from cyclohexanone oxime and high conversion and selectivity for ω-laurolactam produced from cyclododecanone oxime.

22 Claims, 30 Drawing Sheets

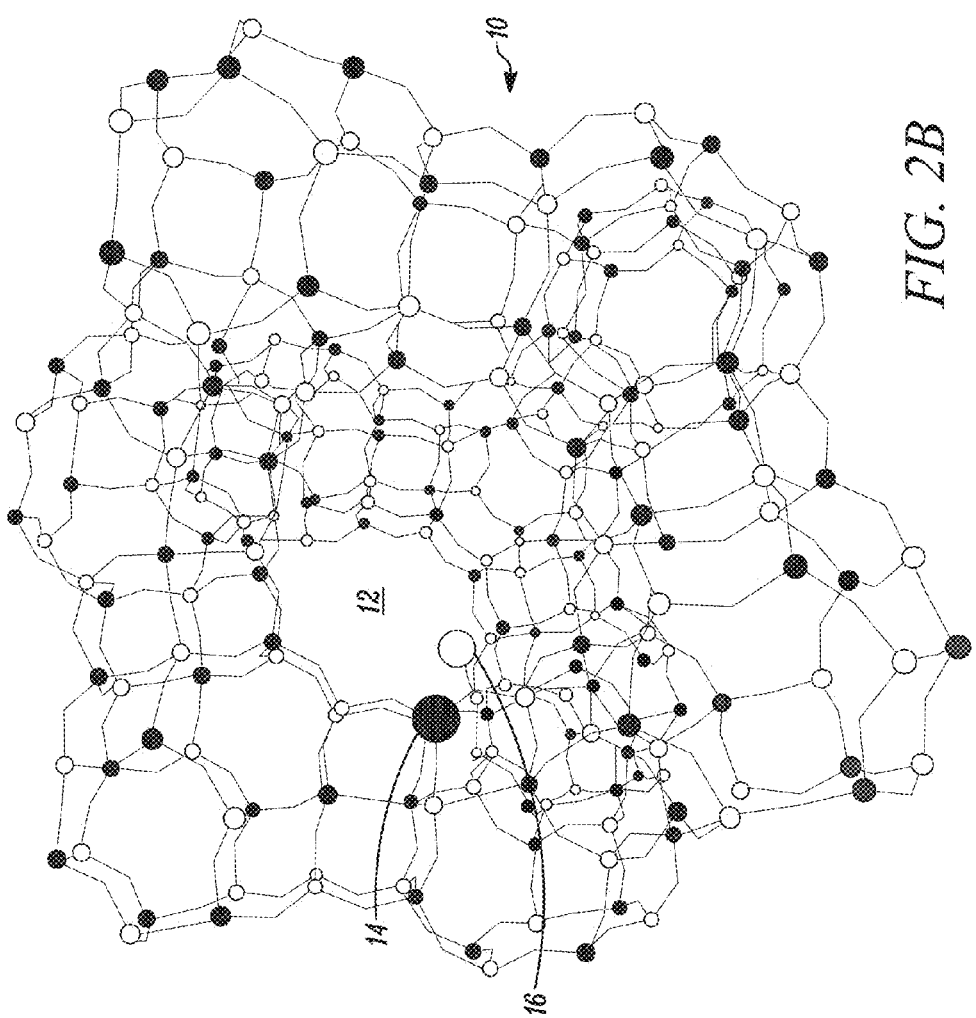

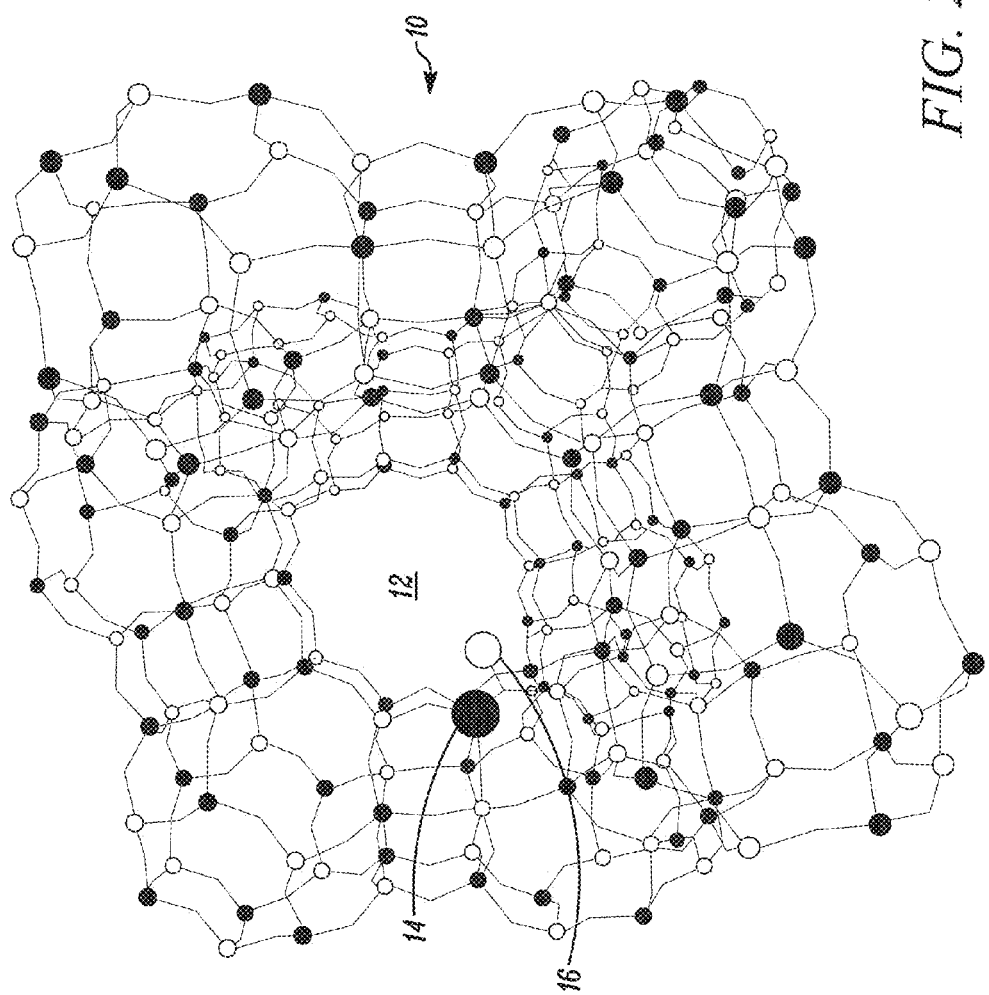

| Sample | Gel Composition | Silicon content/wt% | BET/m²/g | Fd3m unit cell parameter/Å |
|---|---|---|---|---|
| SAPO-37(0.11) | 1.00H$_3$PO$_4$:0.67Al$_2$O$_3$:0.97TPAOH :0.025TMAOH:0.11SiO$_2$ | N/A | N/A | N/A |
| SAPO-37(0.21) | 1.00H$_3$PO$_4$:0.67Al$_2$O$_3$:0.97TPAOH :0.025TMAOH:0.21SiO$_2$ | 2.0 | 588 | 24.31 |
| SAPO-37(0.42) | 1.00H$_3$PO$_4$:0.67Al$_2$O$_3$:0.97TPAOH :0.025TMAOH:0.42SiO$_2$ | 2.7 | 601 | 24.58 |
| SAPO-37(0.63) | 1.00H$_3$PO$_4$:0.67Al$_2$O$_3$:0.97TPAOH :0.025TMAOH:0.63SiO$_2$ | 3.4 | 563 | 24.64 |

SAPO-37(0.21)

GAS AND LIQUID PHASE CATALYTIC BECKMANN REARRANGEMENT OF OXIMES TO PRODUCE LACTAMS

CROSS-REFERENCE TO RELATED APPLICATIONS

This application claims the benefit under 35 U.S.C. §119 (e) of U.S. Provisional Patent Application Ser. No. 61/628, 419 filed Oct. 28, 2011, the disclosure of which is hereby incorporated by reference in its entirety.

FIELD

The present invention relates to methods of producing lactams, such as caprolactam, for example. In particular, the present invention relates to a method producing caprolactam utilizing silicoaluminophosphate (SAPO) catalysts.

BACKGROUND

Traditional approaches for producing lactams, used in the production of nylon, include an oxime undergoing a Beckmann rearrangement in the presence of an acid catalyst, such as fuming sulfuric acid. Exemplary reactions are shown in FIG. 1. As illustrated in FIG. 1A, cyclohexanone oxime is reacted to form ε-caprolactam. ε-caprolactam in turn is polymerized to form Nylon-6. As illustrated in FIG. 1B, cyclododecanone oxime is reacted to form ω-laurolactam. ω-laurolactam in turn is polymerized to form Nylon-12. Nylon-6 and nylon-12 are extensively used in industry and manufacturing.

One potential reaction mechanism for the reaction of FIG. 1A is illustrated in FIG. 1C. The mechanism generally consists of protonating the hydroxyl group, performing an alkyl migration while expelling the hydroxyl to form a nitirilium ion, followed by hydrolysis, tautomerization, and deprotonation to form the lactam.

Typically, Beckmann rearrangement reactions of oximes to form lactams are performed using acids such as fuming sulfuric acid. These reactions are characterized by complete or nearly complete conversion of the oxime and very high selectivity for the desired lactams. However, these reactions also produce byproducts including ammonium sulfate. Although ammonium sulfate is a useful product in itself, minimizing its production may be desirable.

Gas-phase and liquid-phase Beckmann rearrangements of cyclohexanone oximes are known, which employ various natural and synthetic catalysts including solid-acid catalysts. However, the reported results provide low conversion of the oxime and low selectivity of the desired lactam products.

Improvements in the foregoing processes are desired.

SUMMARY

The present disclosure provides methods for producing lactams from oximes by performing a Beckmann rearrangement using a silicoaluminophosphate catalyst. These catalysts are used in gas phase or liquid phase reactions to convert oximes into lactams. High conversion of oxime and high selectivity for the desired lactams are produced using the disclosed methods, including high conversion and selectivity for ε-caprolactam produced from cyclohexanone oxime and high conversion and selectivity for ω-laurolactam produced from cyclododecanone oxime.

In one exemplary embodiment, the present invention provides a method of performing a Beckmann rearrangement reaction. The method comprises reacting an oxime in a liquid phase in the presence of a catalyst to produce a lactam, said catalyst comprising a silicon-containing aluminophosphate with the IZA framework code FAU.

In another exemplary embodiment, the present invention provides another method of performing a Beckmann rearrangement reaction. The method comprises reacting an oxime in a gas phase in the presence of a catalyst to produce a lactam, said catalyst comprising a silicon-containing aluminophosphates with the IZA framework code FAU; wherein said reacting step further comprises the combination of conversion of oxime and selectivity of the lactam is selected from the group consisting of: the conversion of the oxime is at least 50% and the selectivity of the lactam is at least 90%; and the conversion of the oxime is at least 90% and the selectivity of the lactam is at least 80%.

In still another exemplary embodiment, the present invention provides a catalyst. The catalyst comprises a silicon-containing aluminophosphate framework with the IZA framework code FAU; and a plurality of discrete Brønsted acid sites positioned in an interior of the framework, the acid sites comprising silicon isomorphously substituted for phosphorous in the framework; wherein the catalyst is a SAPO-37 type catalyst, and at least 10% of the total number of acid sites are characterized as weak acid sites.

In still another exemplary embodiment, a method of performing a Beckmann rearrangement reaction is provided. The method comprises reacting an oxime in a liquid or gas phase in the presence of a catalyst to produce a lactam, said catalyst comprising a silicon-containing aluminophosphate with the IZA framework code FAU; wherein where the oxime is in a gas phase said reacting step further comprises the combination of conversion of oxime and selectivity of the lactam is selected from the group consisting of: the conversion of the oxime is at least 50% and the selectivity of the lactam is at least 90%; and the conversion of the oxime is at least 90% and the selectivity of the lactam is at least 80%.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

FIGS. 2A-2G illustrate a structures of an exemplary SAPO-37 catalyst;

DETAILED DESCRIPTION

Figure 1A:
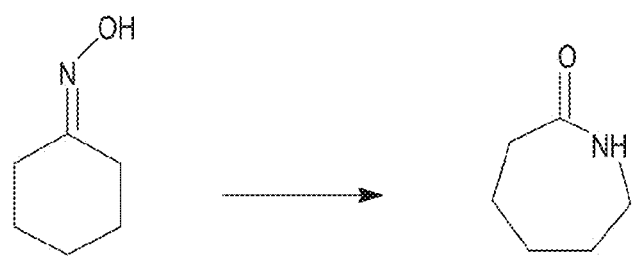
FIG. 1A illustrates the reaction from cyclohexanone oxime to ε-caprolactam.
Figure 1B:
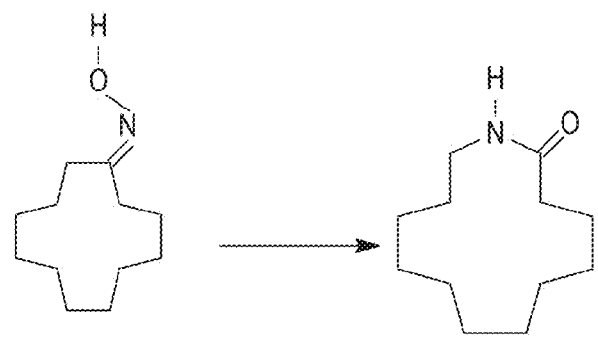
FIG. 1B illustrates the reaction from cyclododecanone oxime to ω-laurolactam.
Figure 1C:
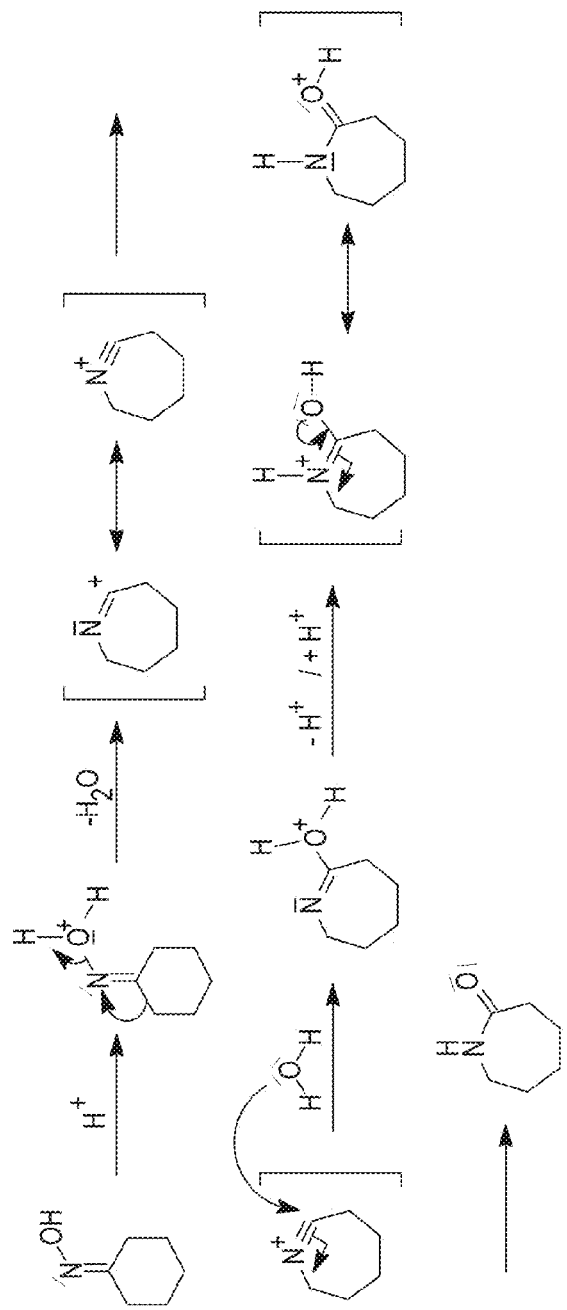
FIG. 1C illustrates the potential steps of a reaction corresponding to a Beckmann rearrangement reaction from cyclohexanone oxime to ε-caprolactam.

The present disclosure is directed to a method to form lactams from cyclic oxime compounds. Exemplary reactions are shown in FIG. 1. As illustrated in FIG. 1A, cyclohexanone oxime is reacted to form ε-caprolactam, which in turn can be polymerized to form Nylon-6. As illustrated in FIG. 1B, cyclododecanone oxime is reacted to form ω-laurolactam, which in turn can be polymerized to form Nylon-12. In other exemplary embodiments, additional lactams besides ε-caprolactam and ω-laurolactam are produced from corresponding oximes via this method. The present method is also useful to perform other Beckmann rearrangement reactions.

The methods according to the present disclosure include an oxime reactant undergoing a Beckmann rearrangement reaction in the presence of a catalyst. Exemplary catalysts include microporous and mesoporous natural and synthetic molecular sieves, zeolites, aluminophosphate (AlPO) materials, and silicoaluminophosphate (SAPO) materials.

Silicoaluminophosphate (SAPO) catalysts are synthetic molecular sieves known to be useful as catalysts. Exemplary methods of preparing certain SAPO catalysts, are provided in U.S. Pat. No. 4,440,871 to Lok, et al., and N. Jappar, Y. Tanaka, S, Nakata, and T. Tatsumi, "Synthesis and Characterization of a New Titanium Silicoaluminophospate: TAPSO-37," Microporous and Mesoporous Materials, Vol. 23, Issues 3-4, August 1998, pp. 169-178, the disclosures of each are hereby incorporated by reference.

Figure 2A:
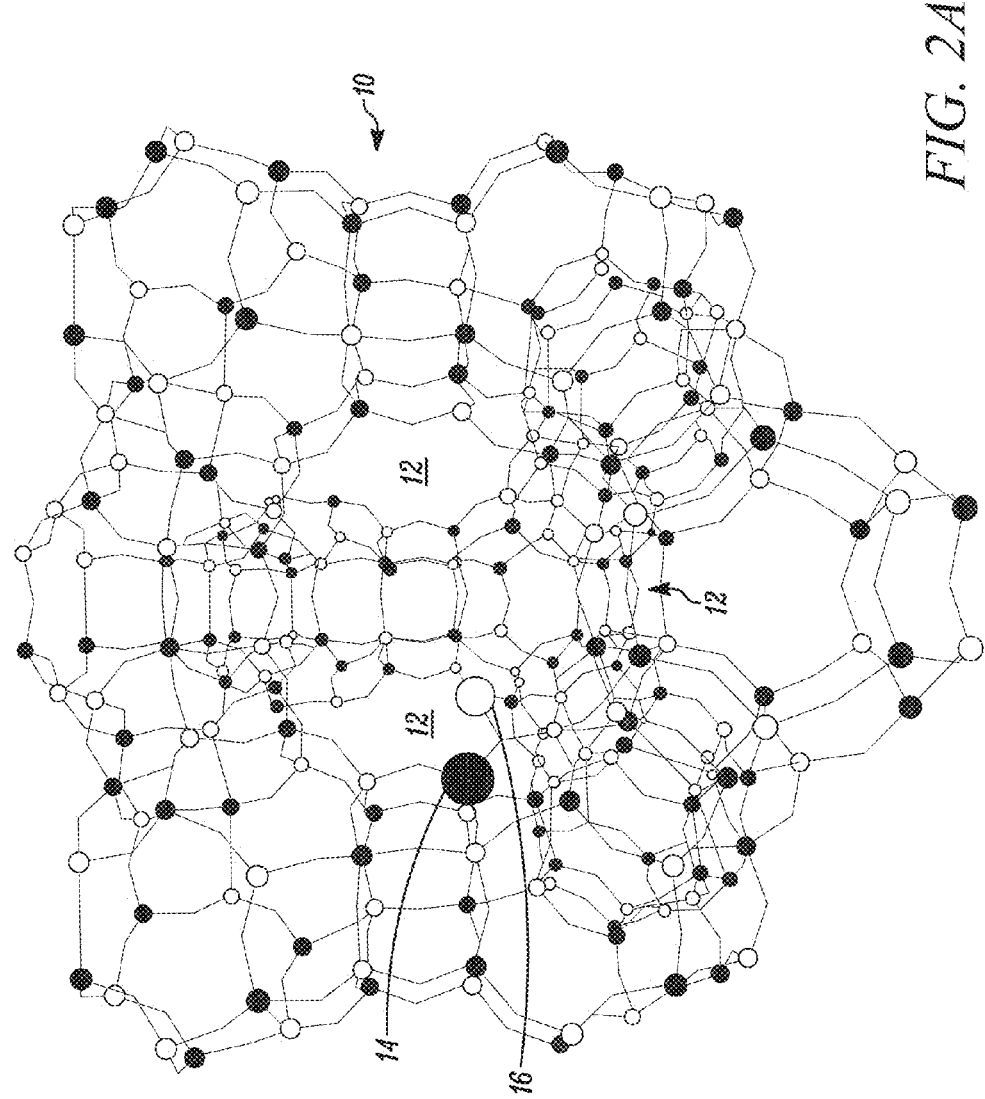
Figure 2C:
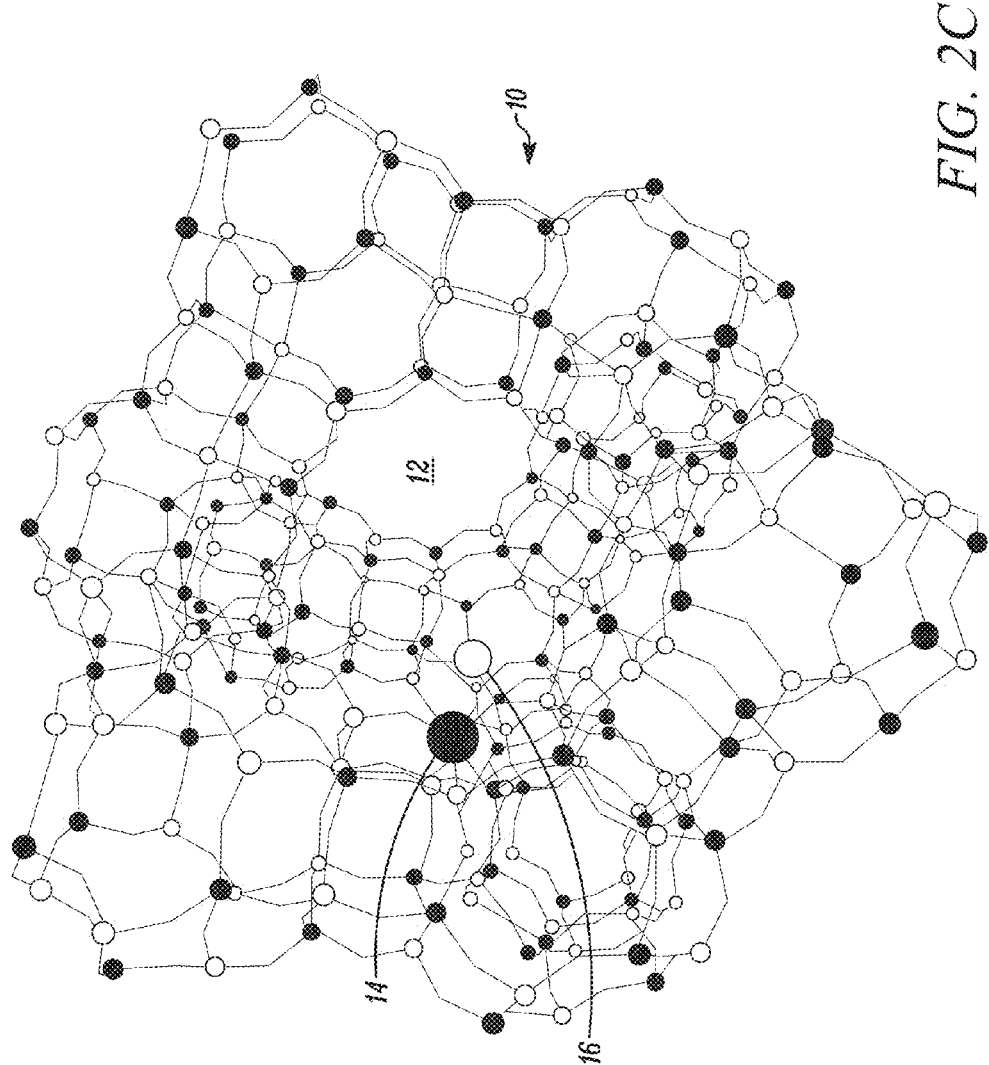
Figure 2E:
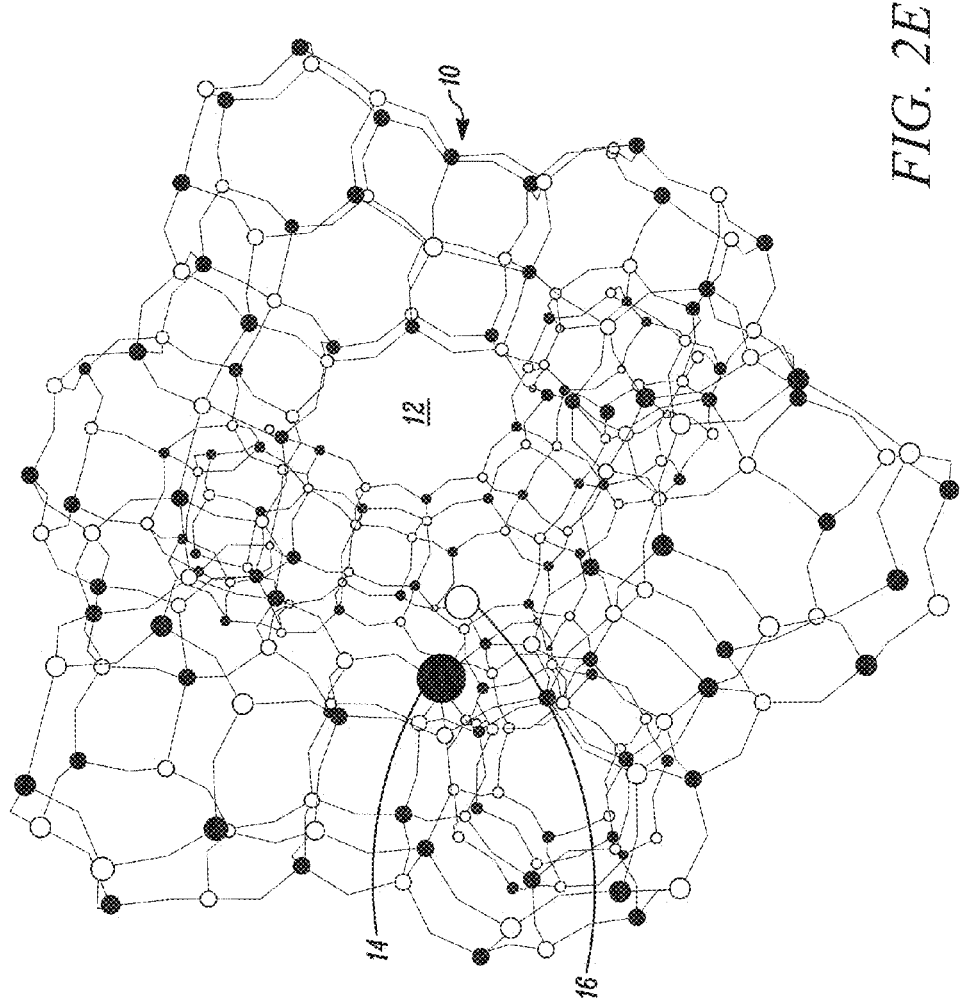
Figure 2F:
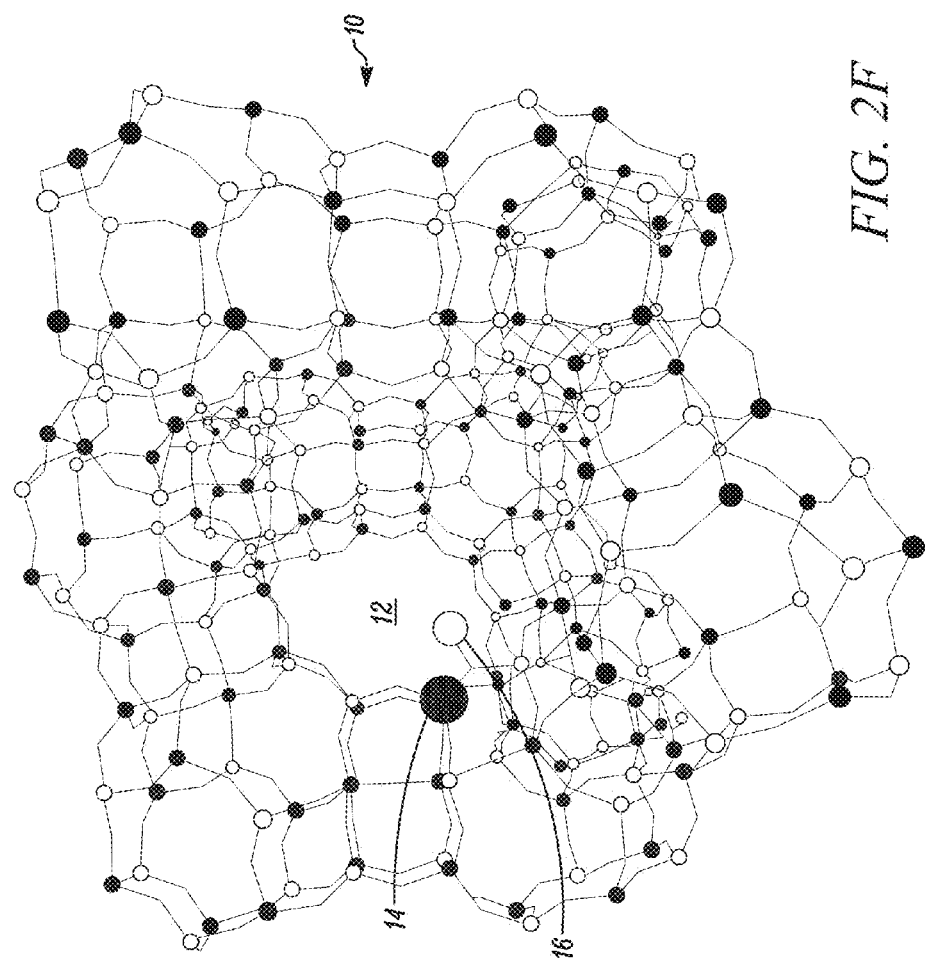

An exemplary structure of one SAPO catalyst, SAPO-37, is illustrated in FIGS. 2A-2G. Molecular sieves, such as the SAPO-37 catalyst illustrated in FIG. 2A, are crystalline structures having a three-dimensional framework of geometries. The frameworks of molecular sieves include cages, cavities, channels, and pores, depending on the type of molecular sieve. Acid sites either on the surface or in the interior or both of the molecular sieve provide the ability for some molecular sieves to act as acid catalysts.

Figure 2G:
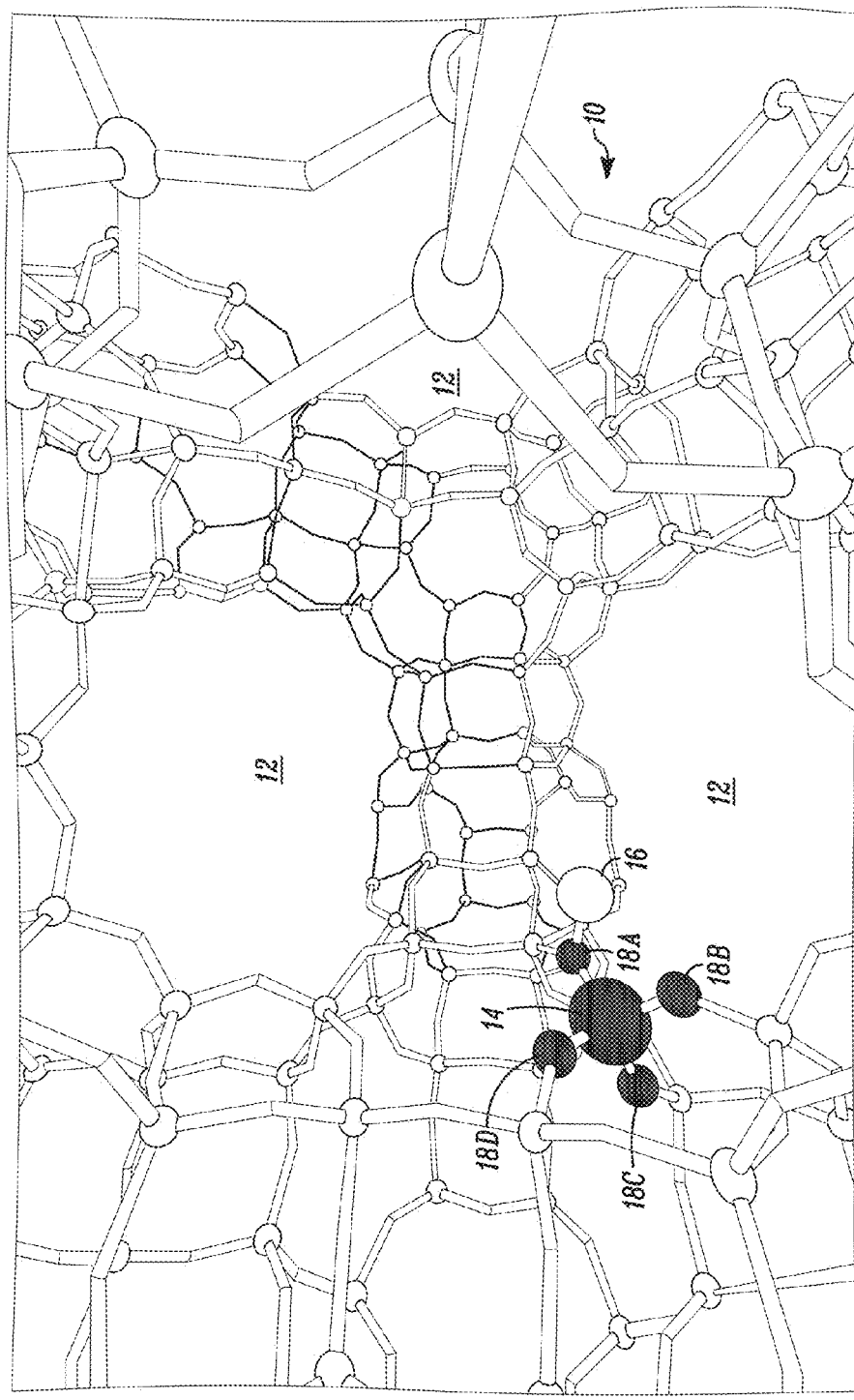

In the exemplary SAPO-37 structure shown in FIGS. 2A-2G, the portion 10 of the catalyst includes a silicon-containing aluminophosphate geometry with a faujasite-type structure. The geometry includes a plurality of pores 12 connecting the interior cavities of the catalyst. FIGS. 2A-2G further illustrate an acid site include a silicon atoms 14 in the interior cavities of the catalyst. The acid sites further include a hydrogen atom, i.e. a proton 16, which is used in catalyzing the Beckmann rearrangement reaction. Silicon atom 14 and proton 16 are enlarged for identification in FIGS. 2A-2G. FIGS. 2A-2F illustrate a variety of perspective views of one interior cavity formed by the catalyst 10. FIG. 2G shows an enlarged view of an acid site including the silicon atom 14 and proton 16 in the interior of the cage formed by the catalyst 10.

As best shown in FIG. 2G, silicon atom 14 is illustratively attached to four oxygen atoms 18A, 18B, 18C, and 18D, indicating it has isomorphously been substituted for a phosphorous atom in the framework of the catalyst. Such an isomorphous substitution is referred to as a type-II substitution. In exemplary embodiments, the catalyst contains a plurality of these isomorphously substituted silicon atoms forming acid sites, such that the acid sites are discrete and well-isolated from each other. This exemplary arrangement allows each acid site to function as a well isolated single-site Brønsted acid. Catalysts having a greater fraction of type II isomorphous substitution acid sites are typified by higher fractions of weak Brønsted acid sites. Higher silicon loaded catalysts are typified by a greater fraction of strong acid sites, which are attributable to type III substitution of two silicon atoms for adjacent aluminum and phosphorous atoms. Type III substitution leads to a reduction in available weak Brønsted acid sites.

Proton 16 is illustratively attached to one of the oxygen atoms 18A. The proton 16 can be given up by the acid site to catalyze a reaction in the cavity, such as a Beckmann rearrangement.

Typically, the catalyst is a silicon-containing aluminophosphate with a faujasite-type structure. In an exemplary embodiment, the catalyst is a silicon-containing aluminophosphate or silicoaluminophosphate catalyst with the International Zeolite Association (IZA) framework code FAU as described in the Atlas of Zeolite Framework Types, 6th ed., Christian Baerlocher, Lynne B. McCusker and David H. Olson, Elsevier, Amsterdam (2007), the disclosure of which is hereby incorporated by reference. More particularly, the catalyst is composed of sodalite cages linked together through 6,6 (double-6) secondary building units. Twelve of these sodalite cages are then used to create a super-cage structure of which the pore-aperture is 7.4 Å and the internal diameter of the super-cage is in the region of 12-14 Å. The catalyst further comprises a plurality of discrete Brønsted acid sites positioned in an interior of the framework, the acid sites comprising silicon isomorphously substituted for phosphorous in the framework;

In exemplary embodiments, the catalyst is a silicoaluminophosphate having a microporous crystalline framework structure and whose essential empirical chemical composition in the as-synthesized form on an anhydrous basis is:

Figure 3A:
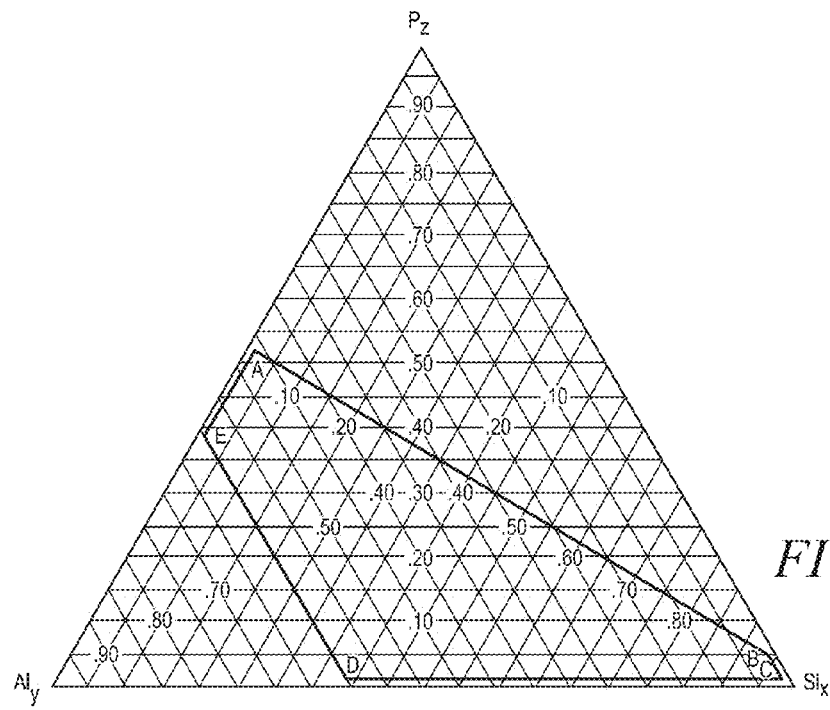
FIG. 3A is a ternary diagram showing the compositional parameters of one embodiment of the silicoaluminophosphates in terms of mole fractions of silicon, aluminum, and phosphorous.

$m$R:(Si$_x$Al$_y$P$_z$)O$_2$ wherein:

R represents at least one organic templating agent present in the intracrystalline pore system;

m has a value of from 0.02 to 0.3;

x, y, and z represent, respectively, the mole fraction of silicon, aluminum, and phosphorous present in the oxide moiety;

in one embodiment, the value of x, y, and z being within the compositional area bounded by points A, B, C, D, and E of the ternary diagram which is FIG. 3A representing the values set forth below in Table 1;

TABLE 1

Mole Fractions Corresponding to FIG. 3A

Figure 3B:
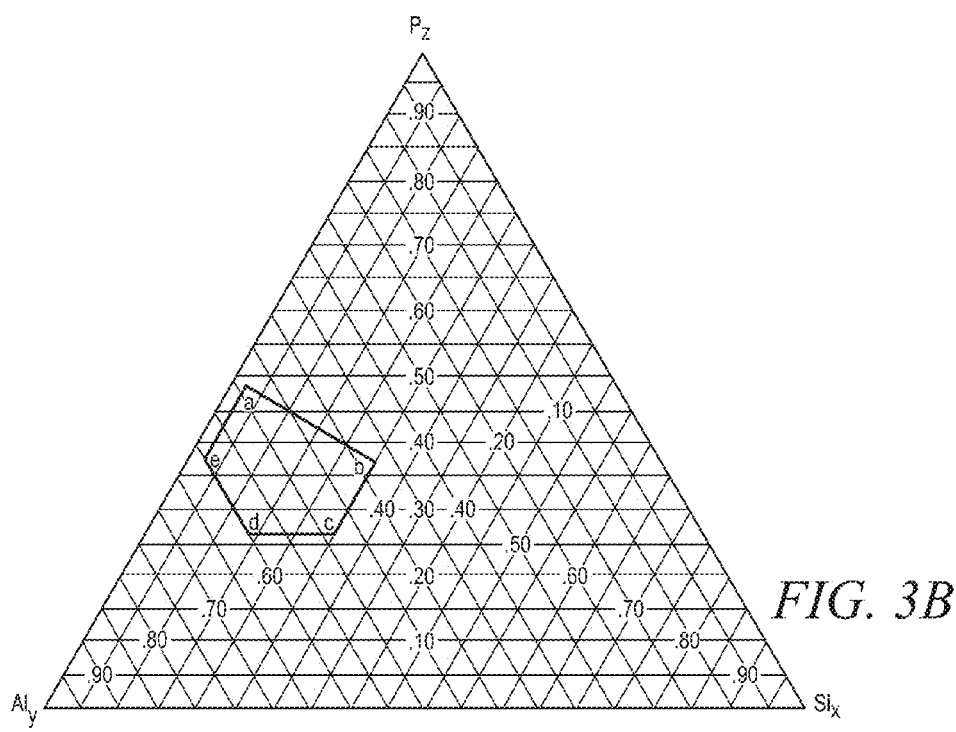
FIG. 3B is a ternary diagram showing the compositional parameters of further embodiments of the silicoaluminophosphates in terms of mole fractions of silicon, aluminum, and phosphorous.

| Point | Mole Fraction | | |
|---|---|---|---|
| | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 | in another embodiment, the value of x, y, and z being within the compositional area bounded by points a, b, c, d, and e of the ternary diagram which is FIG. 3B representing the values set forth below in Table 2;

TABLE 2

Mole Fractions Corresponding to FIG. 3B

| Point | Mole Fraction | | |
|---|---|---|---|
| | x | y | z |
| a | 0.02 | 0.49 | 0.49 |
| b | 0.25 | 0.37 | 0.38 |
| c | 0.25 | 0.48 | 0.27 |
| d | 0.13 | 0.60 | 0.27 |
| e | 0.02 | 0.60 | 0.38 | said silicoalumniophosphate having a characteristic X-ray powder diffraction pattern which contains at least the d-spacing set forth below in Table 3.

TABLE 3

X-ray Powder Diffraction Pattern d-Spacing

| 2θ | d | Relative Intensity |
|---|---|---|
| 6.1-6.3 | 14.49-14.03 | vs |
| 15.5-15.7 | 5.72-5.64 | w-m |
| 18.5-18.8 | 4.80-4.72 | w-m |
| 23.5-23.7 | 3.79-3.75 | w-m |
| 26.9-27.1 | 3.31-3.29 | w-m |

One exemplary procedure for preparation of SAPO-37 catalysts is as follows. First, an aluminum source, such as aluminum oxide, is slowly added to a phosphorous source, such as 85% phosphoric acid. A structural template solution is prepared by dissolving tetramethylammonium hydroxide pentahydrate (TMAOH) in tetrapropylammonium hydroxide (TPAOH), to which fumed silica is slowly added. The solution is then added dropwise with vigorous stirring to the aluminum/phosphorous mixture. The resulting gel is heated to synthesize the desired structure. The resulting product is isolated typically by centrifugation, filtering, and washing. The product is then dried, and calcined, prior to storage in an inert atmosphere.

The relative loadings of silicon and aluminum can be adjusted to provide a suitable quantity and distribution of acid sites on the surface of and in the interior of the catalyst. Exemplary procedures for adjusting the quantity and distribution of acid sites include adjusting the ratio of silicon to phosphorous provided in forming the gel. In typical embodiments, the gel ratio of Si:P is from about 0.1:1 to about 0.8:1. In a more particular embodiment, the gel ratio of Si:P is from about 0.11:1 to about 0.63:1. In still other embodiments, the gel ratio of Si:P is as little as 0.1:1, 0.11:1, 0.16:1, 0.17:1, 0.21:1, 0.22:1, or as great as 0.42:1, 0.63:1, 0.75:1, 0.8:1, or within any range defined between any pair of the foregoing values.

The weight percentage of silicon in the formed catalyst can also be determined. An exemplary method for determining the weight percentage of silicon is by inductively coupled plasma. Typically, silicon comprises from about 1 wt % to about 10 wt % of the total weight of the catalyst. In a more particular embodiment, silicon comprises from about 2 wt % to about 9.1 wt % of the total weight of the catalyst. In still other embodiment, silicon comprises a weight percentage of the total weight of the catalyst up from as little as 1 wt %, 1.5 wt %, 2 wt %, 2.1 wt %, 2.5 wt % to as much as 6 wt %, 7 wt %, 8 wt %, 9 wt %, 9.1 wt %, 10 wt %, or within any range defined between any pair of the foregoing values.

Oximes are converted to lactams, such as in the examples illustrated in FIGS. 1A and 1B, through contact with the catalysts. The present disclosure is believed to be generally applicable to any oxime generated from a variety of aldehydes and ketones. Exemplary oximes include, but are not limited, to cyclohexanone oxime, cyclododecanone oxime, 4-hydroxy acetophenone oxime and oximes formed from acetophenone, butryaldehyde, cyclopentanone, cycloheptanone, cyclooctanone, benzaldehyde.

In exemplary embodiments, the reaction is performed in the presence of a solvent. Although working examples are provided for reactions performed in a solvent, the present disclosure is believed to also be applicable for Beckmann rearrangement reactions performed in the absence of a solvent. In reactions performed in the absence of a solvent, the product is used to absorb the exothermic heat produced by the reaction. In these embodiments, a large ratio of lactam to oxime is maintained in the reaction area to absorb the energy produced by the reaction.

Exemplary solvents include organic nitriles of the formula:

$$R^1-CN$$

Wherein $R^1$ represents $C_1$-$C_8$-alkyl, $C_1$-$C_8$-alkenyl, $C_1$-$C_8$-alkynyl, $C_3$-$C_8$-cycloalkyl; $C_3$-$C_8$-aralkyl including a $O_6$ aromatic ring. Exemplary nitriles include acetonitrile, benzonitrile and mixtures of any of the foregoing.

Other exemplary solvents include aromatic compounds of the formula:

$$R^2-Ar$$

Wherein Ar is an aromatic ring and $R^2$ represents H, F, Cl, or Br. Exemplary aromatic solvents include benzene and chlorobenzene.

Still other exemplary solvents include water and alcohols of the formula:

$$R^3-OH$$

Wherein $R^3$ represents a hydrogen, $C_1$-$C_8$-alkyl, $C_1$-$C_8$-alkenyl, $C_1$-$C_8$-alkynyl, $C_3$-$C_8$-cycloalkyl; $C_3$-$C_8$-arylalkyl. Exemplary alcohols include alcohols of 8 or fewer carbon atoms such as methanol, ethanol, n-propanol, iso-propanol, n-butanol, sec-butanol, isobutanol, tert-butanol, n-amyl alcohol, n-hexanol, phenol, and mixtures of any of the foregoing.

In exemplary embodiments, the solvent is rigorously dried prior to contact with the catalyst. As used herein, rigorously dried is understood to mean dried to a level of 100 ppm water or less. Exemplary methods of drying include adsorption of water using molecular sieves, such as Activated 4A molecular sieves. As used herein, a reaction performed in the absence of water means a reaction in which water comprises less than 0.01 wt % of the weight of the reactants.

The reaction is performed as a liquid phase reaction or a gas phase reaction. As used herein, a liquid phase reaction in a reaction in which substantially all of the oxime is in the liquid phase when reacted to form the lactam. As used herein, a gas phase reaction in a reaction in which substantially all of the oxime is in the gas or vapor phase when reacted to form the lactam.

When performed as a gas phase reaction, the reaction is typically performed at a temperature beneath 350° C. In a more particular embodiment, the reaction is performed at a temperature from about 130° C. to about 300° C. In still other embodiments, the reaction may be performed at a temperature as low as about 90° C., 100° C., 110° C., 120°, 130°, or as high as about 140° C., 150° C., 170° C., 180° C., 190° C., 200° C., 210° C., 220° C., 230° C., 240° C. 250° C., 275° C., 300° C., 325° C., 350° C., or within any range defined between any pair of the foregoing values.

When performed as a gas phase reaction, the reaction is typically performed at a pressure from about 0.1 bar to about 1 bar. More particularly, in exemplary embodiments of the reaction performed as a gas phase reaction, the pressure may be as low as 0.01 bar, 0.02 bar, 0.05 bar, 0.1 bar, as high as 0.5 bar, 1 bar, or within a range defined between any pair of the foregoing values.

When performed as a liquid phase reaction, the reaction is typically performed at a temperature beneath 250° C. In a more particular embodiment, the reaction is performed at a temperature from about 130° C. to about 190° C. In still other embodiments, the reaction may be performed at a temperature as low as about 90° C., 100° C., 110° C., 120°, 130°, or as high as about 140° C., 150° C., 170° C., 180° C., 190° C., 200° C., 210° C., 220° C., 230° C., 240° C. 250° C., or within any range defined between any pair of the foregoing values.

When performed as a liquid phase reaction, the reaction is typically performed at a pressure from about 1 bar to about 5 bar. More particularly, in some exemplary embodiments, the pressure may be as low as 0.5 bar, 1 bar, as high as 1 bar, 2 bar, 5 bar, 10 bar, 15 bar, 20 bar, 25 bar, 30 bar, 35 bar, or within any range defined between any pair of the foregoing values. In some exemplary embodiments of the reaction performed as a liquid phase reaction, the solvent is typically a gas at the reaction temperature, but is maintained in the liquid phase by performing the reaction at an elevated pressure.

When performed as a liquid phase reaction, the reaction is typically performed at a temperature and pressure below the critical point of the solvent, where the pressure may be as low as 1 bar, as high as 2 bar, 5 bar, 10 bar, 15 bar, 20 bar, 25 bar, 30 bar, 35 bar, or within any range defined between any pair of the foregoing values.

The efficiency of the reaction may be expressed in terms of conversion of oxime, selectivity of the desired product, or yield. Conversion is a measure of the amount of oxime reactant that is consumed by the reaction. Higher conversions are more desirable. The conversion is calculated as:

$$\text{Conversion (\%)} = 100\% \times \left(1 - \frac{\text{moles of oxime produced}}{\text{moles of oxime supplied}}\right)$$

Selectivity is a measure of the amount of the desired product that is produced relative to all reaction products. Higher selectivities are more desirable. Lower selectivities indicate a higher percentage of reactant being used to form products other than the desired lactam. The selectivity is calculated as:

$$\text{Selectivity (\%)} = 100\% \times \frac{\text{moles of desired lactam produced}}{\text{total moles of product produced}}$$

Yield is a measurement that combines selectivity and conversion. Yield indicates how much of the incoming oxime is reacted to form the desired lactam. The yield is calculated as:

Yield(%)=Selectivity(%)×Conversion(%)/100%

The methods according to the present disclosure result in high conversions and selectivities.

In typical embodiments, the conversion is 50% or higher. In a more particular embodiment, the conversion is from about 50% to about 100%. For example, the conversion may be as low as about 50%, 60%, 70%, 75%, or as high as about 80%, 85%, 90%, 95%, 97.5%, 99%, 99.5%, approaching 100%, or 100%, or may be within any range defined between any pair of the foregoing values.

In typical embodiments, the selectivity is 50% or higher. In a more particular embodiment, the conversion is as low as about 50%, 55%, 60%, 65%, or as high as about 70%, 75%, 80%, 85%, 90%, 95%, 97.5%, 99%, 99.5%, approaching 100%, or may be within any range defined between any pair of the foregoing values.

In typical embodiments, the conversion of cyclohexanone oxime to ε-caprolactam is from about 90% to about 100% and the selectivity is from about 80% to about 100%. In more particular embodiments, the conversion is from about 95% to about 100% and the selectivity is from about 90% to about 98%. In still more particular embodiments, the conversion is from about 98% to approaching 100% and the selectivity is from about 95% to about 98%.

In typical embodiments, the conversion of cyclododecanone oxime to ω-laurolactam is from about 90% to about 100% and the selectivity is from about 80% to about 100%. In more particular embodiments, the conversion is from about 95% to about 100%, and the selectivity is from about 98% to about 99%.

Example 1

Preparation of SAPO-37 Catalyst

A pseudo-boehmite phase of aluminum oxide was slowly added to a diluted solution of phosphoric acid (85 wt %) and left to stir for 7 hours. A second solution of tetramethylammonium hydroxide pentahydrate (TMAOH) dissolved in tetrapropylammonium hydroxide (TPAOH) (40 wt %) was prepared to which fumed silica was slowly added. This was left to stir for 2 hours and was then added dropwise to a stirred aluminum/phosphorous gel. SAPO-37 catalysts were prepared with four different loadings of $SiO_2$. The catalysts were labeled based on the ratio of $SiO_2$ to $H_3PO_4$ used in the preparation. Gel loadings for the various samples can be found in Table 4 below.

TABLE 4

Gel loadings for SAPO-37 materials

| Sample | Gel composition |
|---|---|
| SAPO-37 (0.11) | $1.00H_3PO_4$:$0.67Al_2O_3$:0.97TPAOH: 0.025TMAOH:$0.11SiO_2$ |

TABLE 4-continued

Gel loadings for SAPO-37 materials

| Sample | Gel composition |
|---|---|
| SAPO-37 (0.21) | $1.00H_3PO_4:0.67Al_2O_3:0.97TPAOH: 0.025TMAOH:0.21SiO_2$ |
| SAPO-37 (0.42) | $1.00H_3PO_4:0.67Al_2O_3:0.97TPAOH: 0.025TMAOH:0.42SiO_2$ |
| SAPO-37 (0.63) | $1.00H_3PO_4:0.67Al_2O_3:0.97TPAOH: 0.025TMAOH:0.63SiO_2$ |

The mixture stirred for 68 hours and was then transferred to an autoclave. The solution was heated under autogeneous pressure at 200° C. for 24 hours. On removal the gel was centrifuged, filtered and washed. The material was then dried overnight at room temperature. The white solid was then calcined at 550° C. for 16 hours and kept in an inert atmosphere.

Example 2

Characterization of Catalysts $^{29}Si$ Solid State NMR

All NMR measurements were performed on a Chemagnetics Infinity 400 spectrometer on a 4 mm magic angle spinning (MAS) double-resonance probe. The sample was packed in a thin wall zirconium oxide rotor and spun at 8 kHz using compressed nitrogen to prevent sample degradation in air. $^{27}Al$ NMR: all experiments were performed using direct acquisition. $^{31}P$ NMR data were acquired both with direct acquisition (120 s delay between scans) and with cross-polarization. $^{29}Si$ NMR data for all 1D experiments were performed using ramped cross-polarization with SPINAL64 decoupling during acquisition. Two dimensional experiments were performed using proton driven spin diffusion (PDSD) with a mixing time of 5 ms.

Figure 4A:
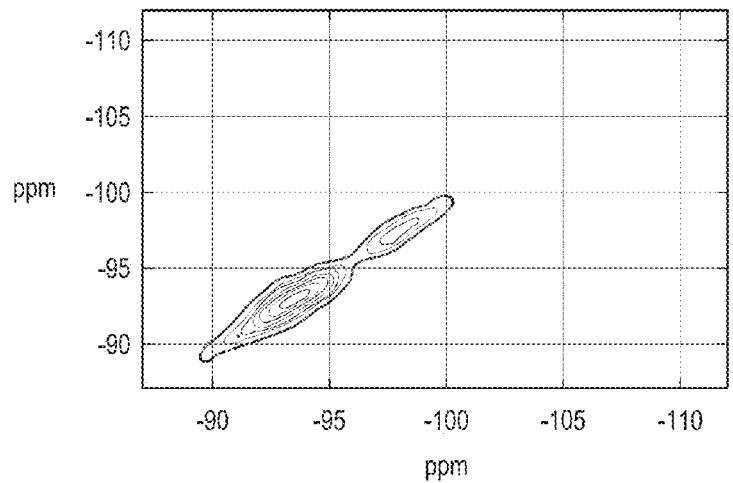
FIGS. 4A-4C correspond to Example 2, and illustrate results from $^{29}Si$ Solid state NMR characterization of SAPO-37 catalysts.
Figure 4B:
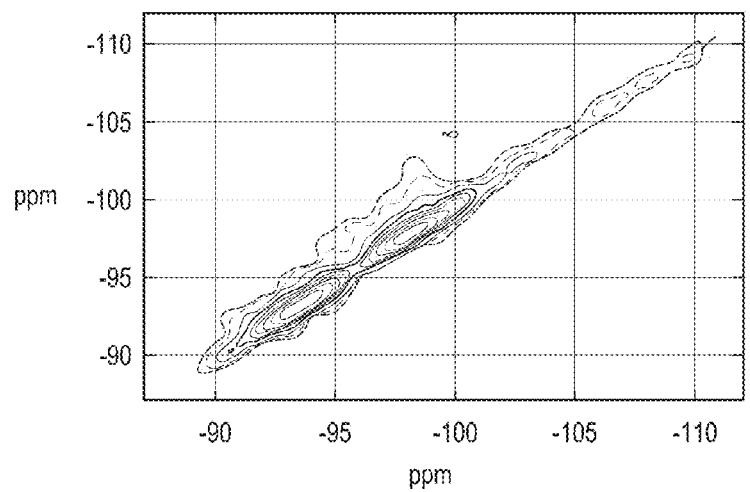
Figure 4C:
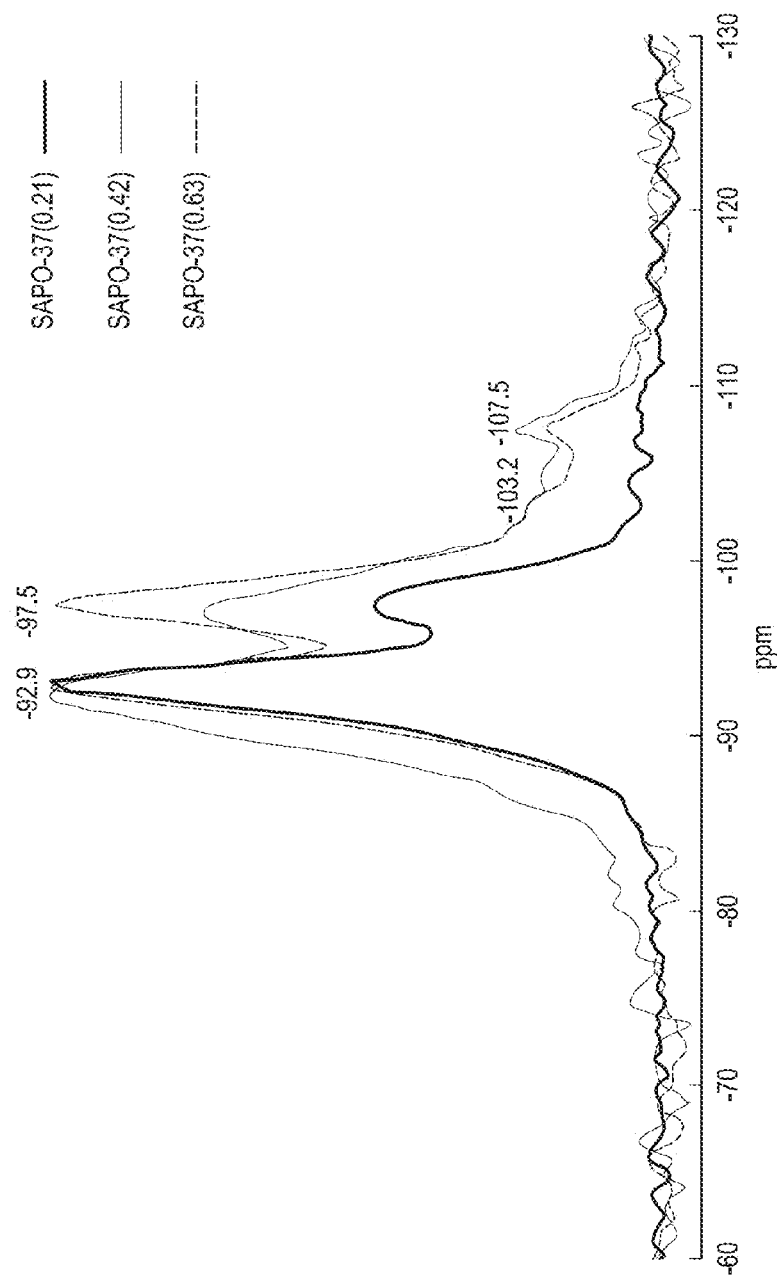

The results of the NMR measurements can be seen in FIG. 4. FIG. 4A shows the results of 2D MAS $^{29}Si$ NMR of SAPO-37(0.21). FIG. 4B shows the results of 2D MAS $^{29}Si$ NMR of SAPO-37(0.63). FIG. 4C shows the results of MAS $^{29}Si$ NMR of SAPO-37 systems of different gel-ratios. FIG. 4C shows the presence of isolated Si(OAl)$_4$ sites at −93 ppm and Si(OAl)$_3$(OSi) sites at −98 ppm.

FIGS. 4A-4C illustrate that silicon begins to cluster at higher loadings. FIG. 4A shows low to no peaks at −103 ppm corresponding to a cluster of two sites, and at −108 ppm, corresponding to a cluster of three sites. As illustrated in FIGS. 4B and 4C, at higher levels of silicon loading, the silicon begins to cluster, forming peaks at −103 ppm—Si(OAl)$_2$(OSi)$_2$ and −108 ppm, Si(OAl)(OSi)$_3$. Lower silicon loadings, such as using SAPO-37 (0.21) as shown in FIGS. 3A and 3C, reduces the peak at −98 ppm, indicating a higher prevalence of isolated single sites with weak Brønsted acidity over clusters of multiple sites.

NH$_3$-Temperature Programmed Desorption (TPD)

The quantity and strength of acid sites was investigated using temperature programmed desorption (TPD) of ammonia. As-synthesized materials were pretreated in a 20% O$_2$ in He mixture and heated at 10° C./min to 550° C. and held at 550° C. for 2 hours. Desorption was performed at 10° C./min to 600° C. for 40 minutes.

In this experiment, ammonia is adsorbed onto the surface of the catalyst, binding to the acid sites, giving a defined peak. The area of this peak corresponds to the quantity of ammonia in the system. The system is then heated and the ammonia desorbs with the temperature. The stronger the acid site, the higher the temperature required to desorb the ammonia.

Figure 5:
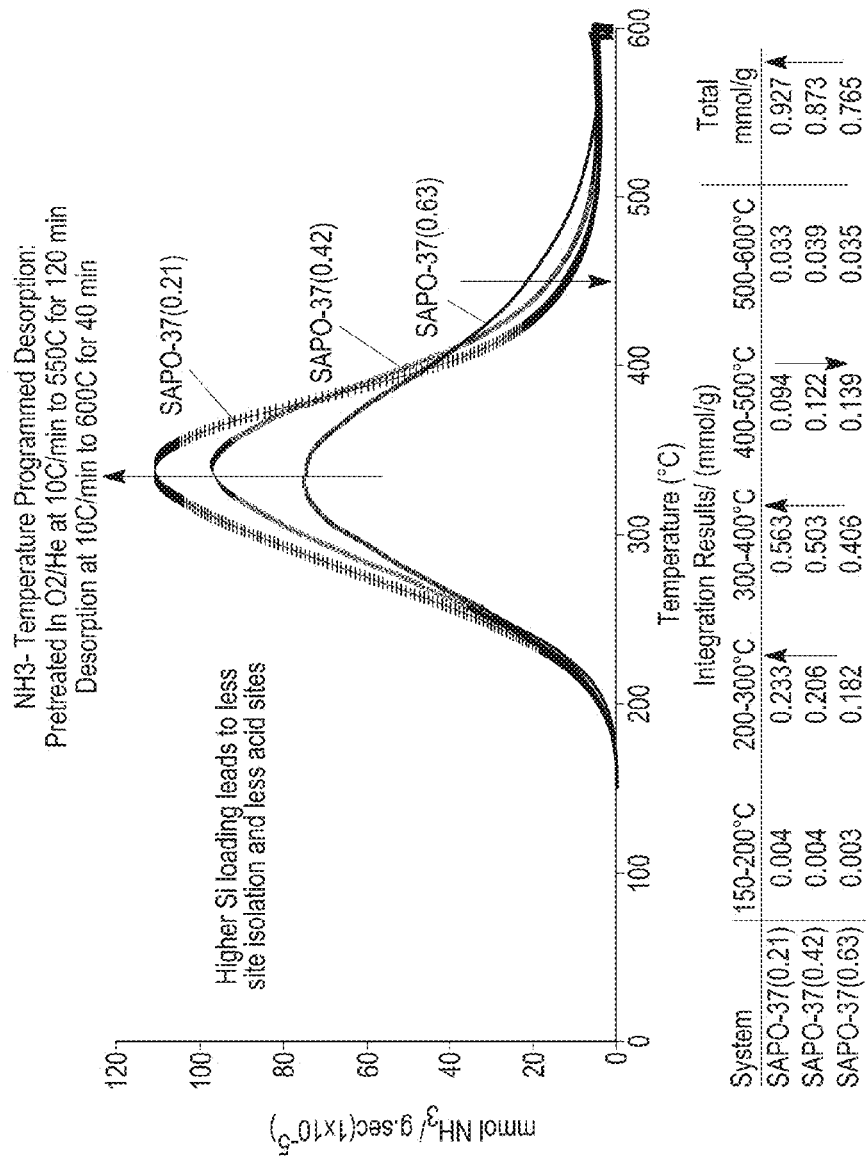
FIG. 5 corresponds to Example 2, and illustrates results from NH$_3$-Temperature Programmed Desorption characterization of SAPO-37 catalysts.

The total acidity values for SAPO-37(0.21) and SAPO-37 (0.42) obtained by NH$_3$-TPD were within experimental error. As shown in FIG. 5, the total number of acid sites, as measured by total mmol/g of desorbed NH$_3$, showed that SAPO-37(0.21) and SAPO-37(0.42) had similar amounts of acid sites, while with SAPO-37(0.63) showed far fewer acid sites than either SAPO-37(0.21) or SAPO-37(0.42). Analyzing the temperature regions indicates the relative strength of the acid sites present, with stronger sites requiring higher temperatures for desorption. As shown in FIG. 5, the lower loading materials SAPO-37(0.21) and SAPO-37(0.42) had more weak acid sites as shown by the higher values at lower temperatures, but increased silicon loading lead to a decrease in weak acid sites and an increase in strong acid sites. These results are consistent with the silicon clustering results suggested by the NMR data in FIGS. 4A-4C.

FT-IR, CO Probe

The number and strength of acid sites were further investigated using FT-IR spectra from a carbon monoxide (CO) probe. Samples of each tested catalyst were ground and pressed into self-supporting pellets. The pellets were then heated at 10° C./min to 550° C. in flowing gas comprising 20% O2/80% N2, then held at temperature for 1 hour. Gas flow was then switched to helium and held for additional 1 hr. The samples were cooled to 30° C. and the spectrum recorded. Nine 0.02 cc injections of CO were added to the samples, followed by 1 final 0.2 cc injection. Following each injection, the system was equilibrated for 3 min before the spectrum was recorded. All spectra were recorded on a Nicolet Nexus 870 IR spectrometer, with 128 scans using a cooled MCT detector. All spectra were processed using the GRAMS/AI 9 software available from Thermo Scientific.

The results of FT-IR, CO probe testing are presented in Table 5.

TABLE 5

FT-IR, CO probe results

| System | CO area/au | Peak shift/cm$^{-1}$ |
|---|---|---|
| SAPO-37(0.21) | 0.854 | 305 |
| SAPO-37(0.42) | 0.856 | 311 |
| SAPO-37(0.63) | 0.582 | 321 |

Table 5 shows that the total acidity, as indicated by the CO area/arbitrary unit (au) is:

SAPO-37(0.21)~SAPO-37(0.42)>SAPO-37(0.63)

The peak shift gives an insight into the acid strength, where a higher shift corresponds to stronger acid sites. Table 5 shows that in terms of acid strength:

SAPO-37(0.63)>SAPO-37(0.42)>SAPO-37(0.21)

Both the NH$_3$-TPD and FT-IR CO probe data suggest that SAPO-37(0.21) has the same quantity of acid sites as SAPO-37(0.42), and that SAPO-37(0.63) has fewer acid sites than either SAPO-37(0.21) or SAPO-37(0.42). Similarly, both the NH$_3$-TPD and FT-IR CO probe data suggest that SAPO-37 (0.63) has the strongest acid sites and SAPO-37(0.21) has the weakest. The NH$_3$-TPD suggested that SAPO-37(0.21) and SAPO-37(0.42) had more weak sites (desorption at 200-300° C. and 300-400° C.) than SAPO-37(0.63), but SAPO-37 (0.63) had more strong acid sites (400-500° C.) than either SAPO-37(0.21) or SAPO-37(0.42).

FT-IR, Collidene Probe

The number and strength of acid sites were further investigated using FT-IR spectra from a collidene probe. Samples were ground and pressed into self-supporting pellets. The pellets were then heated at 10° C./min to 550° C. in flowing 20% O2/N2, then held at temperature for 2 hours. The samples were cooled to 30° C. and the spectrum recorded. Collidene was adsorbed at 150° C. for 1 hr. Collidene was then desorbed at 150/300/450° C. for 1 hr each step. All spectra were recorded on a Nicolet Nexus 870 IR spectrometer, with 128 scans using a cooled MCT detector. All spectra were processed using the GRAMS/AI 9 software available from Thermo Scientific.

In this experiment, collidene is adsorbed onto the surface of the catalyst, binding to the acid sites, giving a defined peak. The area of this peak corresponds to the quantity of collidene in the system. The system is then heated and the collidene desorbs with the temperature. The stronger the acid site, the higher the temperature required to desorb the collidene. Weak sites are characterized as collidene desorbs between 150° and 300° C., medium sites are characterized as collidene desorbs between 300° and 450° C., and strong sites are characterized as still having collidene adsorbed at 450° C.

The results of FT-IR collidene probe testing are presented in Table 6.

TABLE 6

FT-IR, collidene probe results

| System | Weak sites | Medium sites | Strong sites | Total sites |
|---|---|---|---|---|
| SAPO-37(0.21) | 0.913 | 2.845 | 1.609 | 5.367 |
| SAPO-37(0.42) | 0.389 | 2.722 | 1.593 | 4.704 |
| SAPO-37(0.63) | 0.382 | 2.420 | 1.501 | 4.303 |

Table 6 shows that the total acidity as measured by the total number of acid sites is:

SAPO-37(0.63)>SAPO-37(0.42)>SAPO-37(0.21)

Regarding the strength of the acid sites, the weak and medium sites both showed higher numbers for the SAPO-37 (0.21) than SAPO-37(0.63). The large number of weak sites for SAPO-37(0.21), 0.913 out of 5.367 total sites, accounted for more than 15% of the total. This was much higher than for SAPO-37(0.42), which had 0.389 out of 4.704 or 8.3% of the total and SAPO-37(0.63), which had 0.382 out of 4.303 or 8.9% of the total, and suggests a large proportion of Brønsted acid sites that are discrete and of a single-site nature. The strength of the SAPO-37(0.42) weak acid sites and the SAPO-37(0.63) for strong acid sites does not perfectly align with the other acid investigations, but the medium site data is nearly equivalent for SAPO-37(0.21) and SAPO-37(0.42).

The greater fraction of weak Brønsted acid sites is attributable to a greater proportion of type II isomorphous substitutions of silicon for phosphorous in the catalyst framework. Catalysts with higher silicon loadings are typified by greater proportion of strong acid sites that are attributable to type III substitutions, which lead to a reduction in the proportion of weak Brønsted acid sites.

Density Functional Theory (DFT) Characterization

The SAPO-37 unit cell was optimized using CRYSTAL09 package to perform ab initio calculations of crystal system, R. Dovesi, R. Orlando, B. Civalleri, C. Roetti, V. R. Saunders, and C. M. Zicovich-Wilson, Z. Kristallogr. 220, 571 (2005). The SAPO-37 unit cell contained 577 atoms with the formula $H_1Si_1Al_{96}P_{95}O_{384}$. This corresponds to a 1 mol % loading of silicon. A unit cell was modeled with $NH_3$ present such that it could interact with the acid site ($H_4N_1Si_1Al_{96}P_{95}O_{384}$). Using the following equation the binding energy of $NH_3$ with SAPO-37 was estimated to be 117 kJ mol$^{-1}$:

$$E_{bind} = E(\text{SAPO-37} + NH_3) - E(\text{SAPO-37}) - E(NH_3)$$

The above calculation may be used as a measure of acidity. The results are in the expected range for these calculations.

Powder X-ray Diffraction and BET Surface Area

Figure 6:
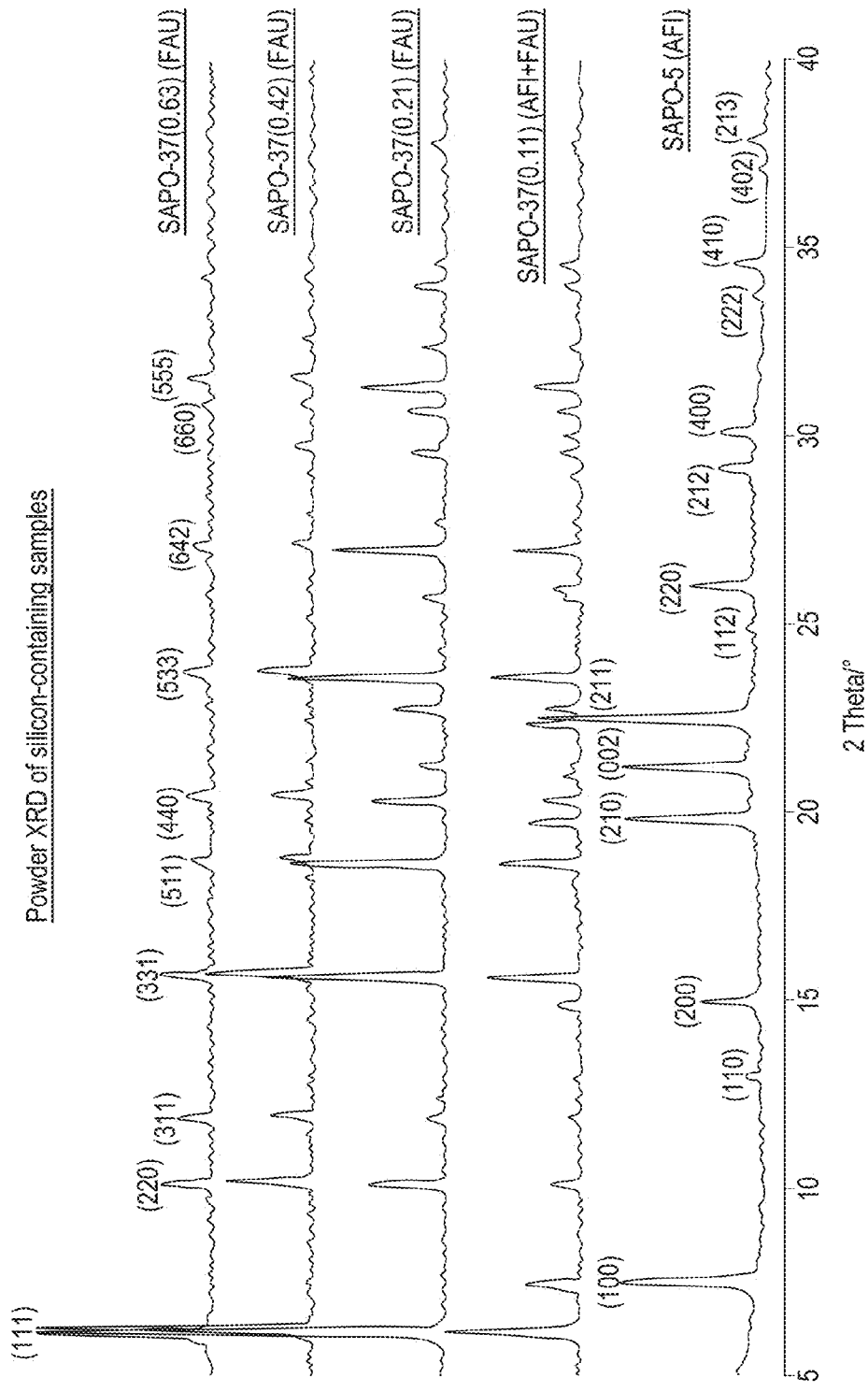
FIG. 6 corresponds to Example 2, and illustrates results from X-Ray Diffraction characterization of SAPO catalysts.

Powder X-Ray diffraction patterns were obtained using a Siemens D5000 diffractometer where λ=1.54056 angstrom (Å) with Cu $K_α1$ radiation. In addition, an X-ray diffraction pattern of the catalyst SAPO-5 (AFI) was obtained. The three higher loading samples were found to be phase-pure, but SAPO-37(0.11) showed a significant AFI impurity phase. The SAPO-37(0.11) showed peaks corresponding to both FAU-type framework at 111 and 331, as well as IZA AFI-type framework at 100 and 200. The results of powder X-ray diffraction can be found in FIG. 6.

Figures 7, 8A:
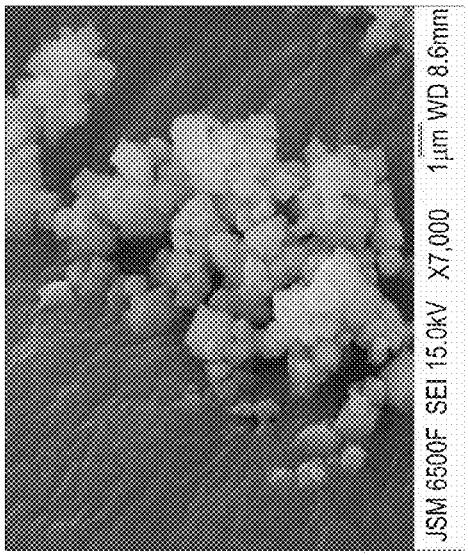
FIG. 7 corresponds to Example 2, and illustrates results from BET surface area characterization of SAPO-37 catalysts.
FIGS. 8A-8C correspond to Example 2, and are SEM pictures of SAPO-37 catalysts.

BET surface area measurements to investigate the total surface area of the catalysts were performed using a Gemini 2375 surface area analyzer and prepared using flow gas preparation. The results of BET surface area measurements and estimated silicon content in wt % can be found in FIG. 7. The unit cell determinations provided similar unit cell sizes for the three measured SAPO-37 catalysts, although the larger loadings of $SiO_2$ resulted in slightly larger unit cells, providing additional evidence for increased silicon substitution in the molecular sieve framework.

The XRD and BET results were typical for this system.

Inductively Coupled Plasma (ICP)

ICP measurements were taken to quantify the actual weight percentage of silicon in each of the prepared catalyst. A Perkin-Elmer Optimum 3000 DV was used to provide ICP results. Calcined samples were prepared and fully digested in 10 ml of deionized water and 10 ml of ACS Plus Certified sulfuric acid available from Fisher Scientific. Solutions of standard concentrations were used for calibration.

The ICP results and ratio of silicon to phosphorous loadings in the gel formed in Example 1 can be found in Table 7 below:

TABLE 7

ICP results

| System | Si/P Gel ratio from synthesis gel | Si/wt % From ICP measurements |
|---|---|---|
| SAPO-5(AFI) | 0.21 | 1.33 |
| SAPO-34(CHA) | 0.23 | 0.73 |
| SAPO-BER | 0.21 | 0.73 |
| SAPO-37(0.21) | 0.21 | 2 |
| SAPO-37(0.63) | 0.63 | 9.1 |

The ratio of silicon to phosphorous in the gel used to form the catalysts for SAPO-37(0.63) and SAPO-37(0.21) was 0.63:0.21, or 3:1. The silicon weight percentage of SAPO-37 (0.63) was higher than the silicon weight percentage of SAPO-37(0.21). The ratio of silicon weight percentage between SAPO-37(0.63) and SAPO-37(0.21) was 9.1:2, or 4.55:1. This was higher than the gel loading ratio of 3:1.

Scanning Electron Microscopy Images

Figure 8C:
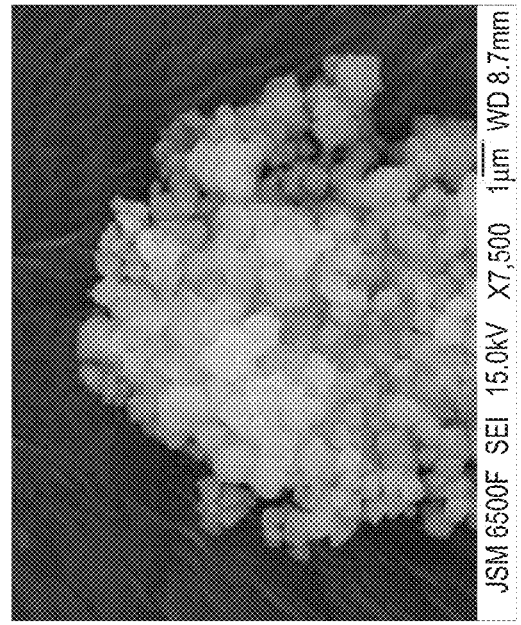
Figure 8B:
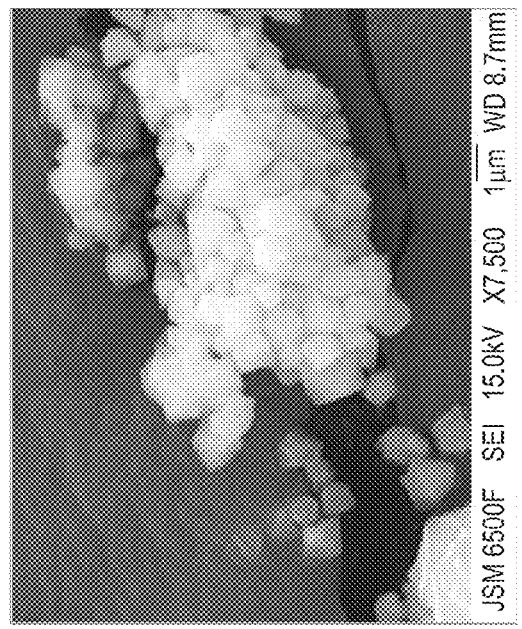

Scanning Electron Microscopy images of the catalysts were obtained using a JOEL-JSM5910 microscope with accelerating voltage of 0.3-30 kV. The samples were prepared by gold coating. SEM revealed that all 3 systems consisted of regular octahedral crystals of roughly 1 μm in length. An SEM image of SAPO-37(0.21) is provided as FIG. 8A, an SEM image of SAPO-37(0.42) is provided as FIG. 8B, and an SEM image of SAPO-37(0.63) is provided as FIG. 8C.

Example 3

Gas Phase Catalysis

Preparation of Catalysts

The gel loadings for the catalysts used in the gas phase examples is given in Table 8.

TABLE 8

Gel loadings for SAPO materials

| Sample | Gel composition |
|---|---|
| SAPO-5 | $2.0H_3PO_4:1.0Al_2O_3:0.4SiO_2:$<br>$2.0Triethylamine:50.0H_2O$ |
| HSAPO-37 (0.42) | $1.00H_3PO_4:0.67Al_2O_3:0.97TPAOH:$<br>$0.025TMAOH:0.42SiO_2$ |
| MSAPO-37 (0.22) | $1.00H_3PO_4:0.69Al_2O_3:2.40TPAOH:$<br>$0.026TMAOH:0.22SiO_2:6.96H_2O$ |
| LSAPO-37 (0.17) | $1.00H_3PO_4:0.68Al_2O_3:2.40TPAOH:$<br>$0.026TMAOH:0.17SiO_2:7.12H_2O$ |
| SAPO-11 | $2.0H_3PO_4:1.0Al_2O_3:0.4SiO_2;$<br>$2.0Pr_2NH:50.0H_2O$ |
| SAPO-41 | $2.0H_3PO_4:1.0Al_2O_3:0.4SiO_2;$<br>$2.0Pr_2NH:50.0H_2O$ |

The SAPO-37 catalysts were made as in Example 1.

SAPO-5 was prepared by diluting 4.7 g of $H_3PO_4$ (85% in $H_2O$) in a Teflon beaker with 10 ml of $H_2O$ and stirred until homogeneous (5 minutes). 4.3 g of $Al(OH)_3$ was slowly added to the acid, followed by a further 10 ml of $H_2O$. The mixture was stirred for 10 minutes. 0.76 g of fumed silica was slowly added, followed by 10 ml of $H_2O$. The mixture was stirred for 30 minutes. Finally the templating agent (N-Methyl-dicyclohexyl-amine) was added dropwise and a further 10 ml of $H_2O$ was added. The mixture was stirred for 1 hour. The white gel was then transferred to an autoclave and heated to 200° C. for 2 hours. On removal, the gel was filtered and washed with $H_2O$ and left to dry at 70° C. overnight. The white solid produced was calcined at 550° C. for 10 hours before use.

SAPO-TRY was prepared in the same manner as the SAPO-5 above, except that no templating agent was used.

The SAPO-34 catalyst was prepared according to the method provided by D. Dubois, et al., *Fuel Process. Technol.* 2003, 83, 203, the disclosures of which are hereby incorporated by reference.

TS-1, a titanium silicalite zeolite-based catalyst was obtained from the National Chemical Laboratory, Pune India. The sample has a Ti loading of 2 wt %. The TS-1 catalyst is disclosed in U.S. Pat. No. 4,859,785, the disclosure of which is hereby incorporated by reference.

Analysis of Conversion and Selectivity

The conversion and selectivity of the system was analyzed using a Clarus 400 gas chromatogram with FID and using an Elite 5 column, the peak areas were calibrated using known response factors. The method was: start at 120° C., hold for 2 minutes, then ramp at 15° C./min up to 220° C., and hold for 5 minutes at 220° C. The method was 13 minutes and 40 seconds long in total. The cyclohexanone oxime has a peak corresponding to a retention time of 4.0 minutes, ε-caprolactam peak has a peak corresponding to a retention time of 5.8 minutes, the by-product has a peak corresponding to a retention time of 6.6 minutes. The injector port was set to 220° C. and the detector was set to 250° C. The carrier pressure (Helium) was 14 psig. The method was given 1 minute to equilibrate before injection. A centrifuged sample of 5 μl was injected.

The samples were calibrated using a relative response factor of ε-caprolactam relative to cyclohexanone oxime, which was found to be 1.119. The samples were calibrated to an internal standard of chlorobenzene for the mass balance. Cyclohexanone oxime was found to have a relative response factor of 1.2972 relative to chlorobenzene, and ε-caprolactam was found to have a response factor of 1.4516 relative to chlorobenzene. The mass balance at 130° C. was found to be 106% after 6 hours. Using the following formula, the response factors were used to calculate the moles of cyclohexanone oxime, ε-caprolactam, and by-products (response factor assumed to be 1.00):

$$\frac{\text{Moles}[A]}{\text{Moles}[B]} = \text{Relative Response Factor} \times \frac{\text{Area}[A]}{\text{Area}[B]}$$

Experimental Procedure

A cylindrical glass tube (4 mm in diameter) with a glass frit was packed with a 5 mm layer of glass beads, a layer of pelletized catalyst (~0.25 g, 40 mm) and a further 60 mm layer of glass beads, was placed inside a flow reactor heated by a jacket to 673 K. The sample was then treated under a flow of Helium gas for 1 hour. The temperature was dropped to the test temperature as set forth below and a liquid feed of 10 wt % cyclohexanone oxime in ethanol was fed into the reactor, maintaining the experimental weight hour space velocity (WHSV) as set forth below.

Comparison of Catalysts at WHSV 0.3 $hr^{-1}$ and 300° C.

Gas phase runs were made for various catalysts under similar conditions. The conditions selected were a WHSV of 0.3 $hr^{-1}$, a liquid feed of 10 wt % oxime in ethanol, a temperature of 300° C., helium flow of 33.3 mL/min, and 0.25 g of catalyst. Each catalyst was pre-activated at 400° C. for 1 hour in a 33.3 mL/min flow of helium. Samples were taken for conversion and selectivity analysts after an hour.

Figure 9:
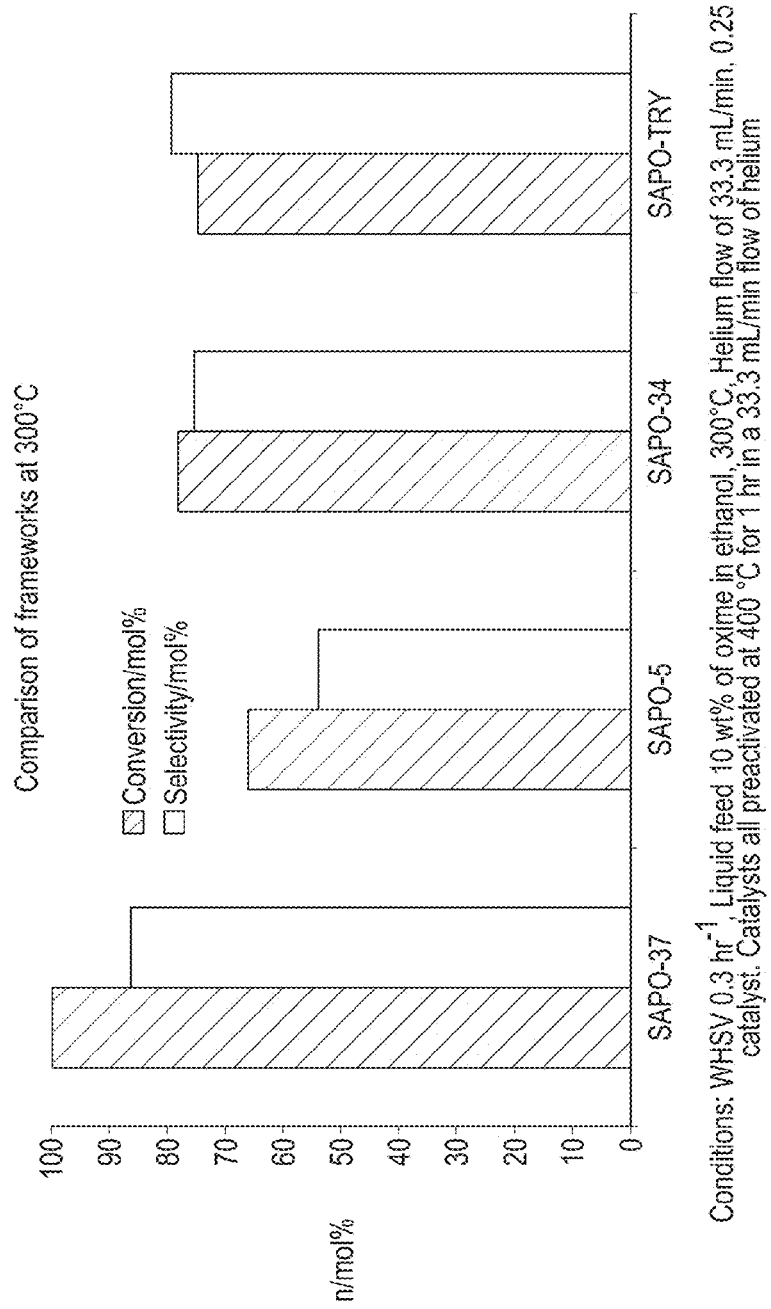
FIGS. 9-15 correspond to Example 3, and illustrate the conversion and selectivity results of gas phase Beckmann rearrangement reactions of cyclohexanone oxime to ε-caprolactam using various catalysts.

The results can be found in Table 9 and FIG. 9.

TABLE 9

Gas phase results

| System | Conversion/mol % | ε-caprolactam selectivity/mol % |
|---|---|---|
| SAPO-37 (0.42) | 99.7 | 86.2 |
| SAPO-5 | 66.0 | 53.8 |
| SAPO-34 | 78.2 | 75.2 |
| SAPO-TRY | 74.9 | 79.0 |

The SAPO-37 (0.42) catalyst produced much higher conversion and selectivity results than any of the other SAPO catalysts tested.

Comparison of SAPO-37 Catalysts with SAPO-41 and TS-1 at Various Temperatures

As a comparison, gas phase runs were made for SAPO-37, SAPO-41, and TS-1 catalysts under similar conditions. The conditions selected were a WHSV of 0.3 $hr^{-1}$, a liquid feed of 10 wt % oxime in ethanol, a helium flow of 33.3 mL/min, and 0.25 g of catalyst. Each catalyst was pre-activated at 400° C. for 1 hour in a 33.3 mL/min flow of helium. Samples were taken for conversion and selectivity analysts after an hour. The results for various temperatures are provided in FIGS. 10-13.

Figure 10:
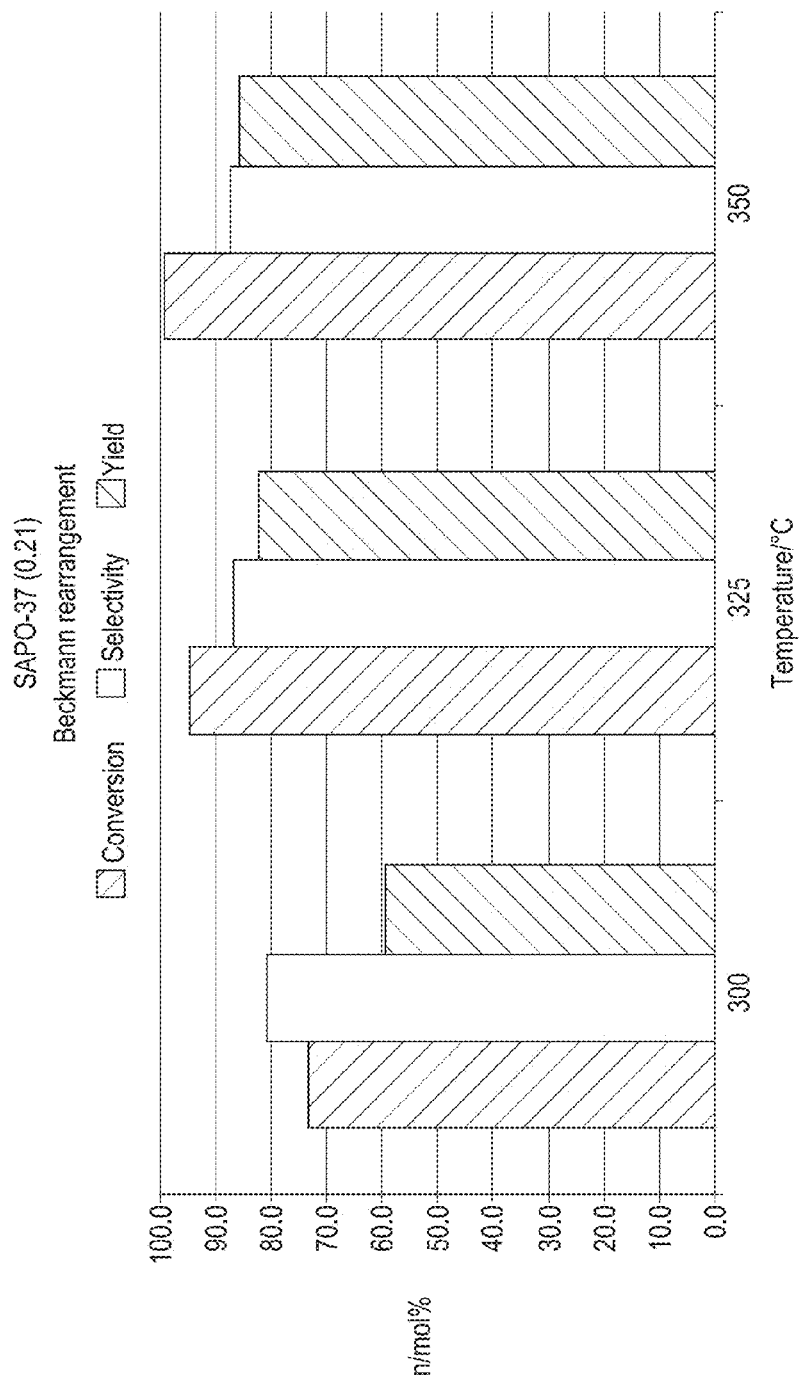

The results for SAPO-37(0.22) are shown in FIG. 10. SAPO-37(0.22) resulted in high conversions and selectivity. Conversion increased as temperature increased from 300° to 350°. Selectivity also increased, but was above 80% in at all three measured temperatures.

Figure 11:
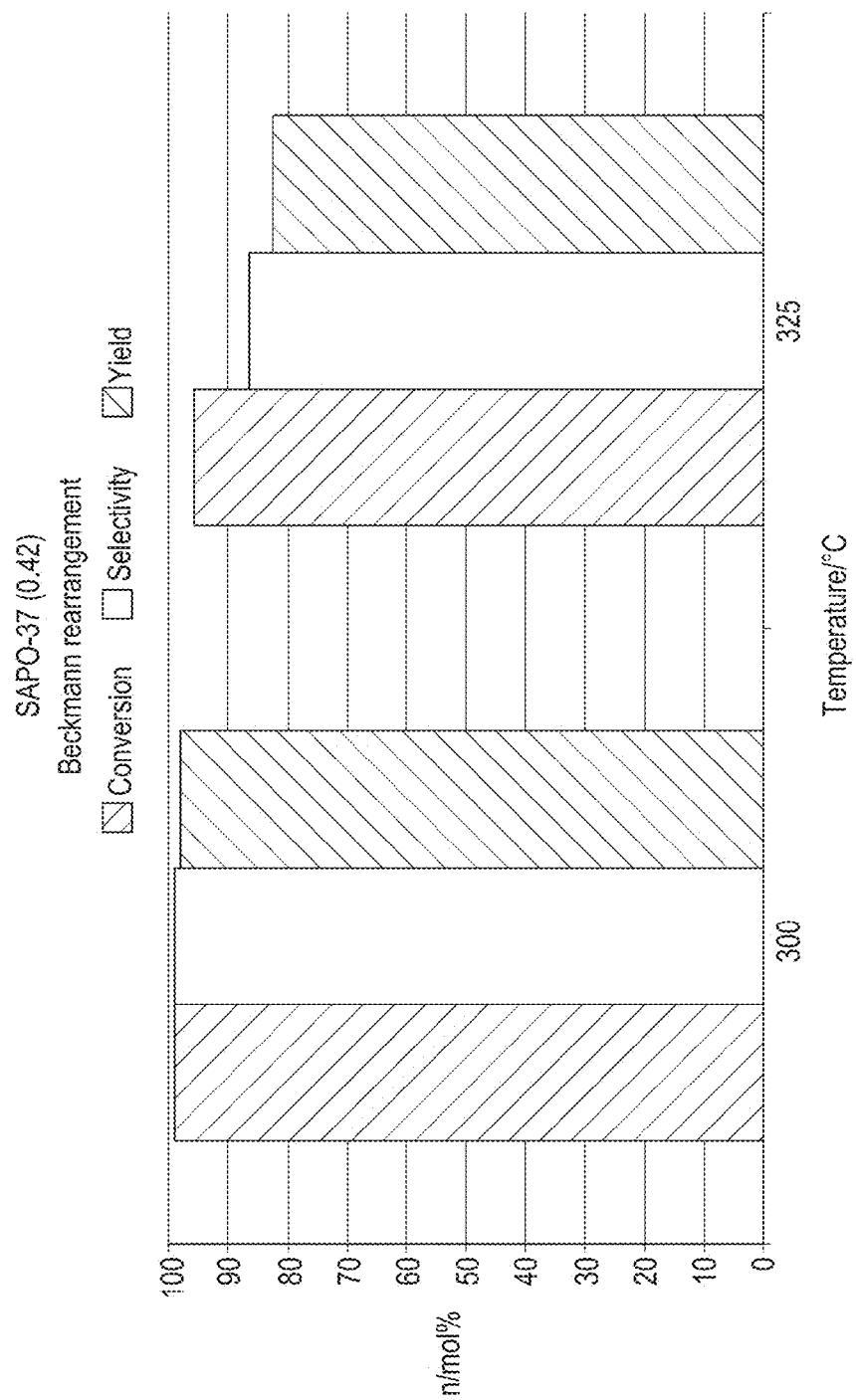

The results for SAPO-37(0.42) are shown in FIG. 11. SAPO-37(0.22) resulted in high conversions and selectivity. Conversion and selectivity decreased as temperature increased from 300° to 325°. However, conversion remained high at 94.6% and selectivity remained above 80%.

Figure 12:
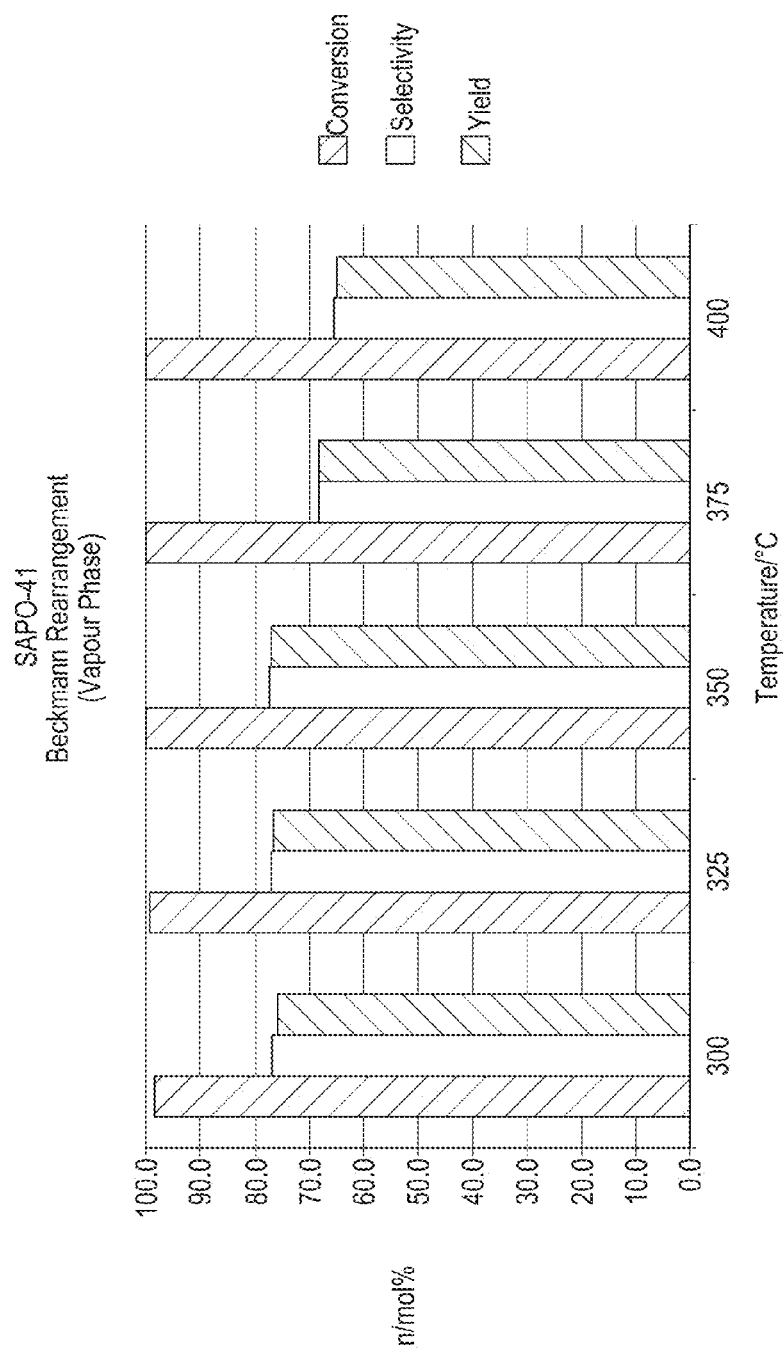

As shown in FIG. 12, the SAPO-41 provided high conversion, but much lower selectivity to the ε-caprolactam than the SAPO-37 catalysts.

Figure 13:
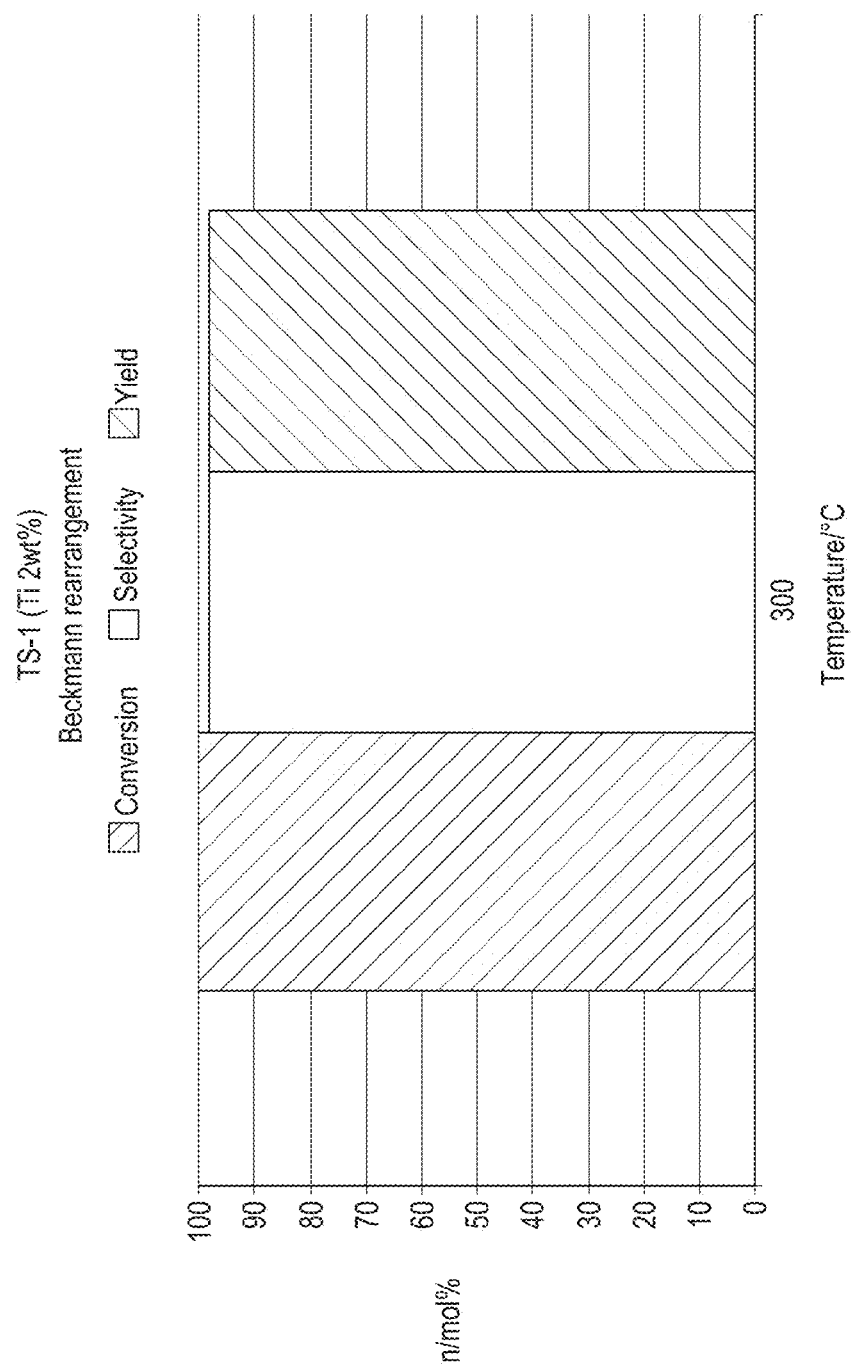

The results for TS-1 are shown in FIG. 13. Conversion and selectivity were high for TS-1 at 300° C.

Figure 14:
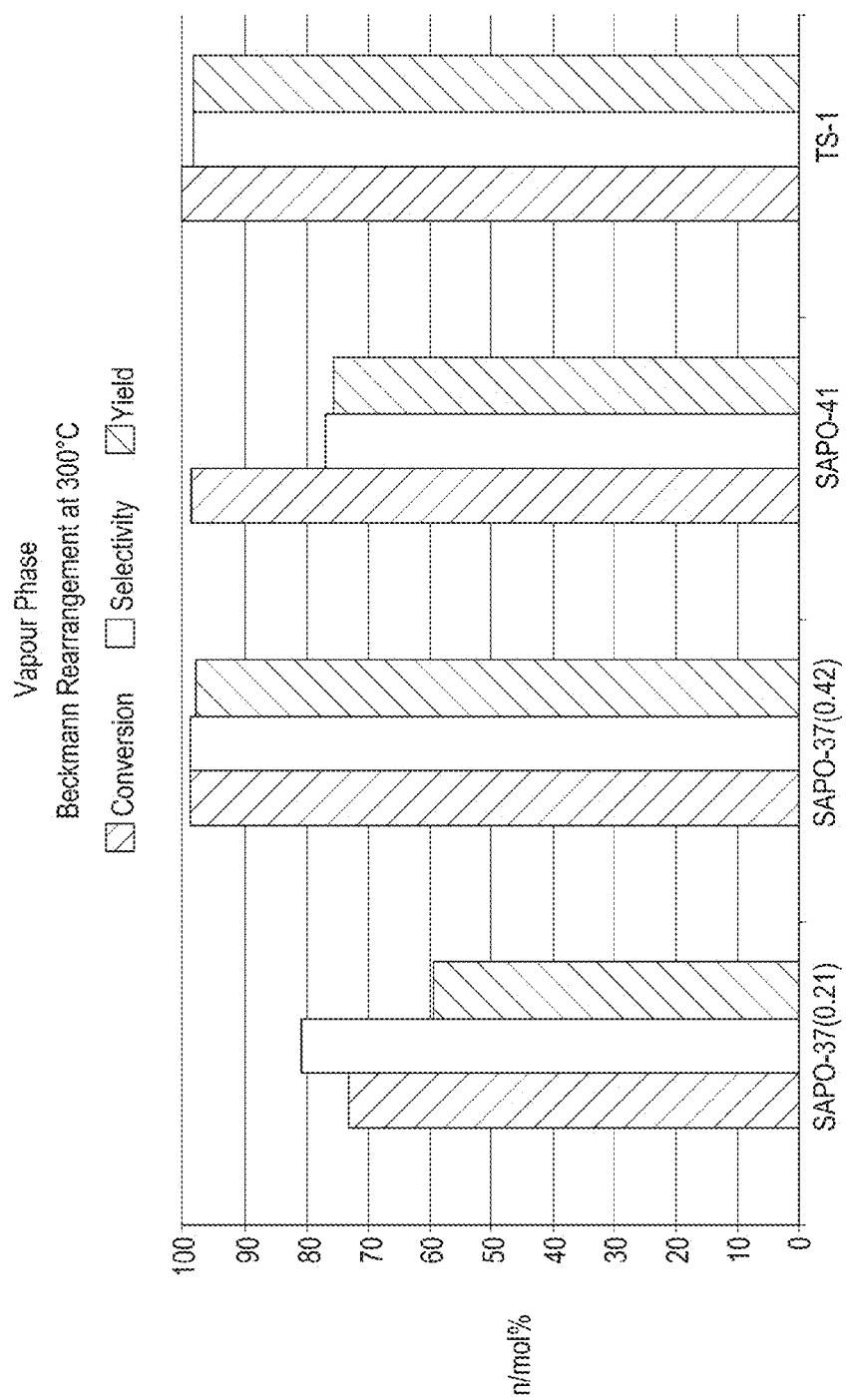
Figure 15:
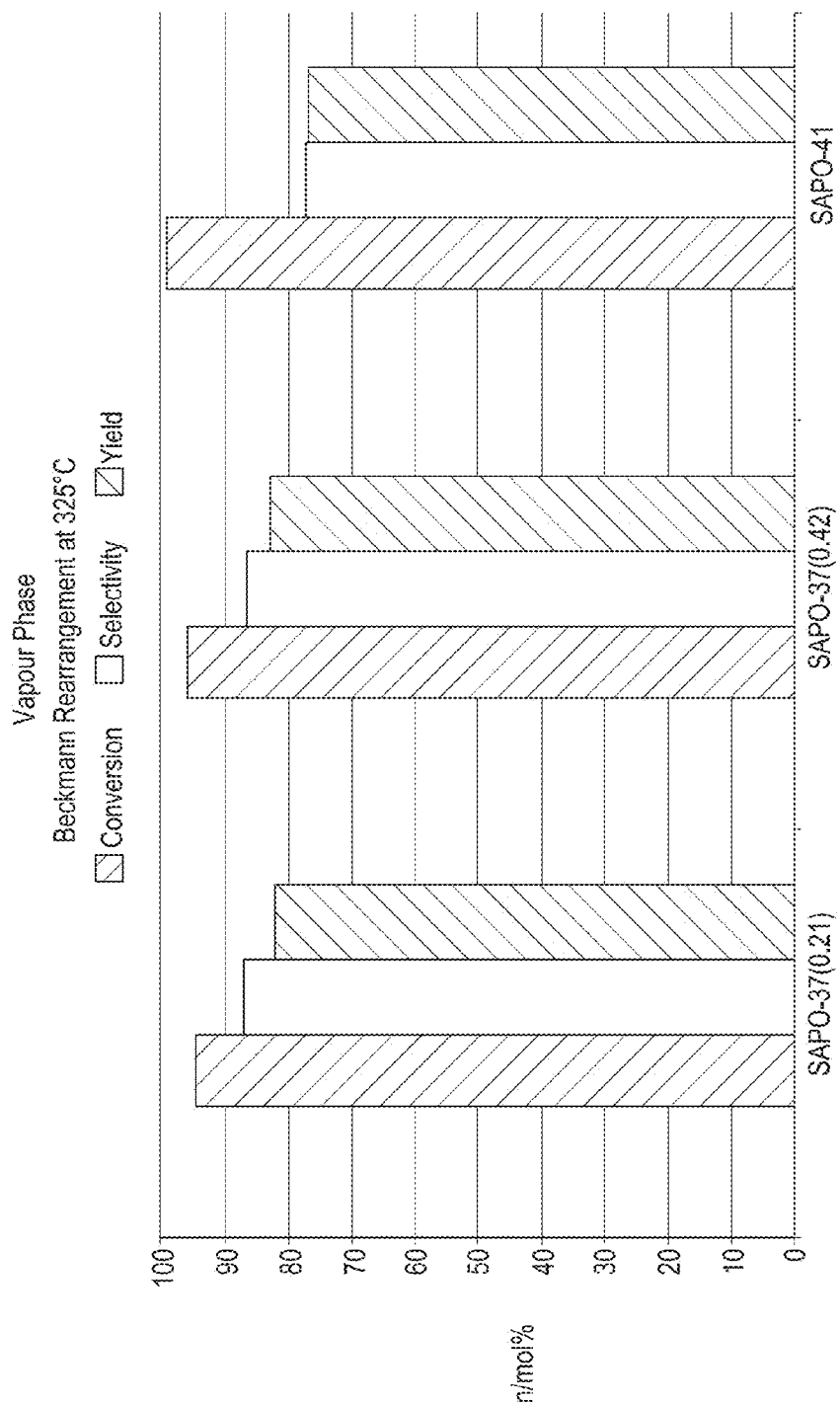

FIGS. 14 and 15 compare the results from the various catalysts at the same temperatures.

As can be seen in FIG. 14, at 300° C., high selectivity and conversion were obtained for SAPO-37(0.42) compared to the SAPO-41 catalyst.

As shown in FIG. 15, all three SAPO catalysts gave good conversion at 325° C. However, only the SAPO-37 catalysts gave high selectivities.

Example 4

Liquid Phase Catalysis

Preparation of Catalysts

The gel loadings for the catalysts used in the gas phase examples is given in Table 10.

TABLE 10

| Sample | Gel composition |
|---|---|
| Gel loadings for SAPO materials | |
| SAPO-5 | $2.0H_3PO_4:1.0Al_2O_3:0.40SiO_2:2.0TEA:50H_2O$ |
| SAPO-34 (CHA) | $2.0H_3PO_4:1.0Al_2O_3:0.30SiO_2:2.0TEAOH:50H_2O$ |
| SAPO-37 (0.21) | $1.00H_3PO_4:0.67Al_2O_3:0.97TPAOH:0.025TMAOH: 0.21SiO_2$ |
| SAPO-37 (0.42) | $1.00H_3PO_4:0.67Al_2O_3:0.97TPAOH:0.025TMAOH: 0.42SiO_2$ |
| SAPO-41 | $2.0H_3PO_4:1.0Al_2O_3:0.4SiO_2; 2.0Pr_2NH:50.0H_2O$ |

The SAPO-37 catalysts were made as in Example 1.

The SAPO-5 and SAPO-34 catalysts were made as in Example 3.

The SAPO-11 catalyst was made according to P. Meriaudeau, V. A. Tuan, V. T. Nghiem, S. Y. Lai, L. N. Hung and C. Naccache, *Journal of catalysis*, 1997, 169, 55-66, the disclosure of which is hereby incorporated by reference.

The SAPO-41 catalyst was made according to P. Meriaudeau, V. A. Tuan, V. T. Nghiem, S. Y. Lai, L. N. Hung and C. Naccache, *Journal of catalysis*, 1997, 169, 55-66, the disclosure of which is hereby incorporated by reference.

Experimental Procedure 100 mg of cyclohexanone oxime, 100 mg of catalyst and 20 ml of benzonitrile as solvent (Aldrich) were added to a glass reactor and stirred at 500 rpm at the selected temperature under reflux. Samples were taken at predetermined intervals based on the selected temperature: 30 minutes for 130° C., 15 minutes for 150° C., 5 minutes for 170° C., and 5 minutes for 190° C. All samples were analysed on a Varian Star 3400CX gas chromatogram with flame ionization detector (FID). Samples were injected into a Perkin Elmer a HP1 cross linked methylsiloxane (30 m×0.32 mm×1 μm film thickness) column. The samples were mass balanced using chlorobenzene as an internal standard.

Analysis of Conversion and Selectivity

The samples were analyzed as in Example 3, with benzonitrile solvent peak having a large peak corresponding to a retention time of 3.5 minutes.

Comparison of Catalysts at 130° C.

Liquid phase runs were made for various catalysts under similar conditions. The conditions selected were 130° C., with a catalyst:cyclohexanone oxime:benzonitrile ratio of 1:1:200, and 0.1 g of cyclohexanone oxime. The samples were analyzed after 7 hours.

Figure 16:
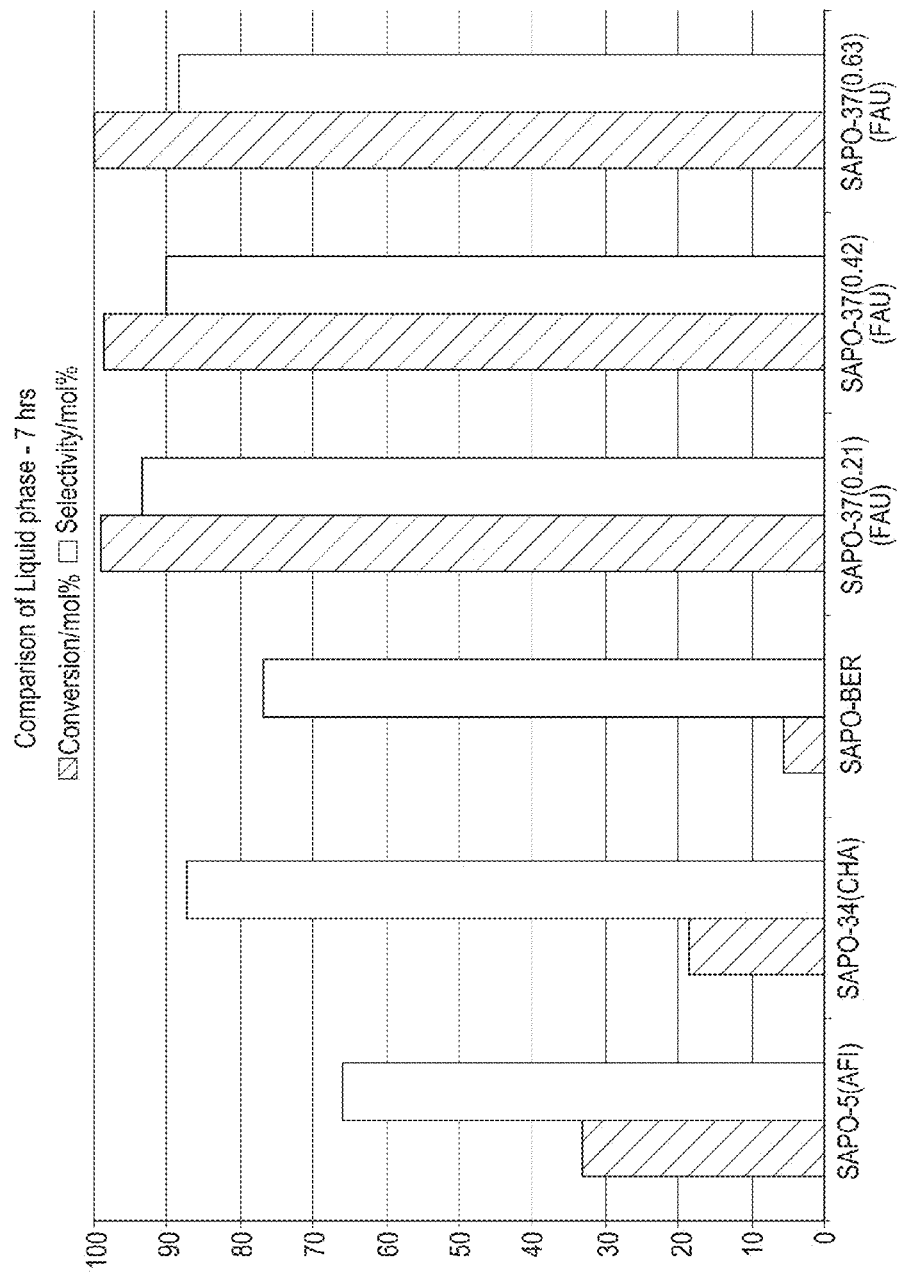
FIGS. 16-20 correspond to Example 4, and illustrate the conversion and selectivity results of liquid phase Beckmann rearrangement reactions of cyclohexanone oxime to ε-caprolactam using various catalysts.

The results can be found in Table 11 and FIG. 16.

TABLE 11

| | Liquid phase results | | | |
|---|---|---|---|---|
| System | IZA framework code | Pore diameter | Conversion/ mol % | ε-caprolactam selectivity/ mol % |
| SAPO-5 | AFI | 7.3 Å × 7.3 Å | 33.2 | 65.9 |
| SAPO-34 | CHA | 3.8 Å × 3.8 Å | 18.6 | 87.3 |
| SAPO-37 (0.42) | FAU | 7.4 Å × 7.4 Å | 98.8 | 90.3 |
| SAPO-41 | AFO | 7.0 Å × 4.3 Å | 23.5 | 68.1 |

The SAPO-37 and SAPO-5 frameworks have similar pore diameters, the former 7.4 Å, the latter 7.3 Å, yet they showed very different levels of activity, therefore the environments were probed using $^{29}Si$ MAS NMR techniques. The SAPO-37 spectrum showed a dominant peak at −93 ppm, with a smaller secondary peak at −98 ppm, corresponding to $Si(OAl)_4$ and $Si(OSi)(OAl)_3$ environments respectively. The $Si(OAl)_4$ environment shows that the silicon has substituted a single phosphorus atom, therefore generating a Brønsted acid site (a type II substitution mechanism), the $Si(OSi)(OAl)_3$ environment shows that two silicons have substituted a phosphorus and aluminium pair, therefore not generating an acidity (type III substitution mechanism). In contrast the SAPO-5 spectrum showed a dominant peak at −110 ppm, corresponding to a $Si(OSi)_4$ environment, suggesting the silicon was present mostly in siliceous zones. This showed that the isolated silicon sites are the active site for this reaction. The silicon content of the SAPO-37 species was varied (denoted SAPO-37(X) where X is the as-synthesised gel ratio), giving three different samples, which showed subtle differences in catalytic performance.

Both SAPO-37 catalysts showed very high conversion and selectivity, especially when compared to the other SAPO catalysts.

Liquid Beckmann Rearrangement Using Chlorobenzene Solvent

The same experimental procedure as for the liquid reactions with benzonitrile were performed with chlorobenzene as a solvent. The reaction was performed at 130° C., with 100 mg of cyclohexanone oxime, 100 mg of SAPO-37(0.21) catalyst, and 20 ml of chlorobenzene. After 7 hours, 14.6% conversion of oxime and 95.0% selectivity for ε-caprolactam were observed.

Progression of Reaction Over Time for Various Catalysts at 130° C.

The conversion, selectivity, and yield over time of a reaction with a SAPO-37 (0.16) catalyst, a SAPO-11 catalyst, and a SAPO-41 catalyst at 130° C. are illustrated in FIGS. 17-20. The SAPO-37 catalyst showed very high conversion and selectivity compared to the other SAPO catalysts.

Figure 17:
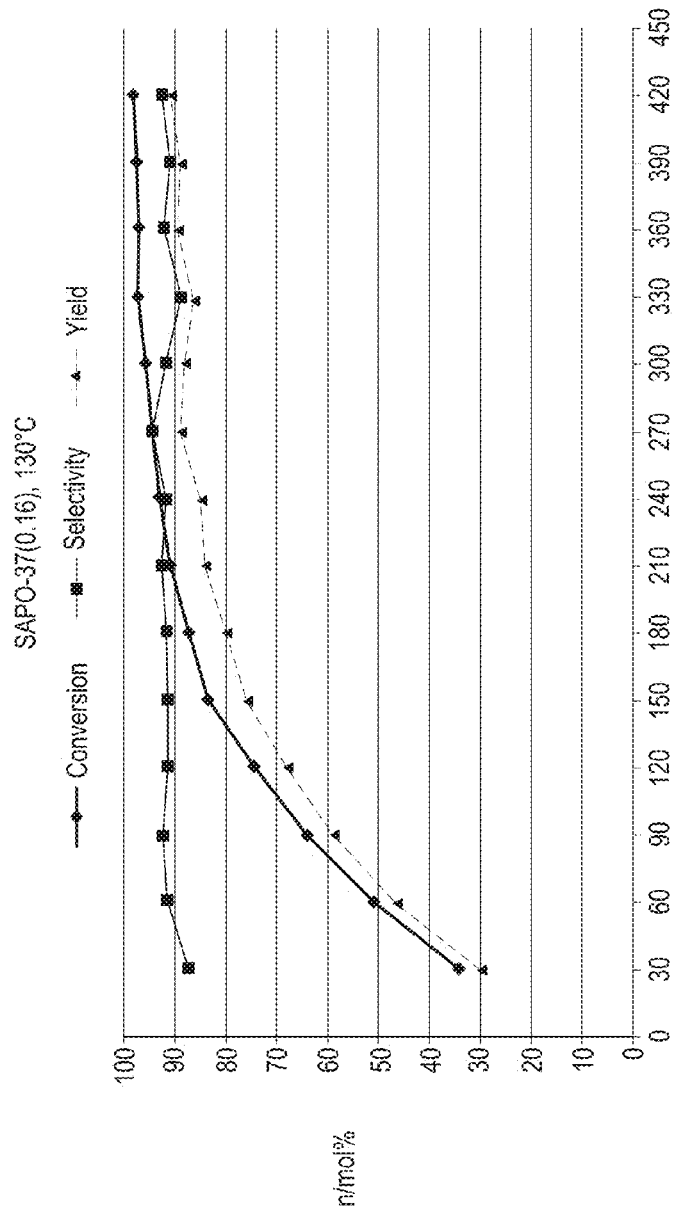

FIG. 17 illustrates the high conversion and selectivity using the SAPO-37 (0.16) catalyst in a liquid phase reaction using benzonitrile as solvent. The reaction was performed at 130° C., with a catalyst:cyclohexanone oxime:benzonitrile ratio of 1:1:200, with 0.1 g of cyclohexanone oxime used, and performed for 7 hours.

Figure 18:
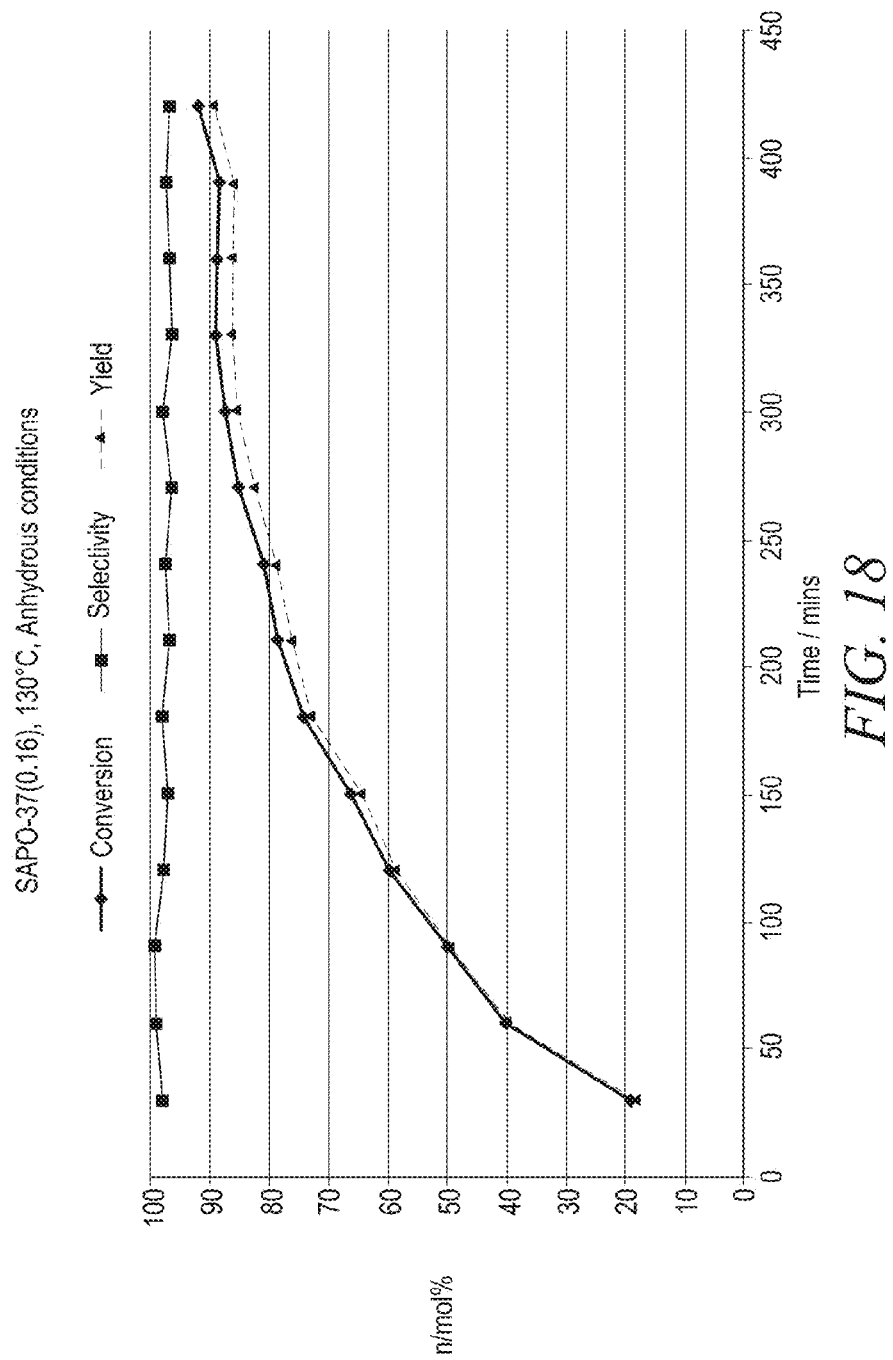

FIG. 18 illustrates the same reaction using anhydrous benzonitrile as solvent. The reaction was performed at 130° C., with a catalyst:cyclohexanone oxime:anhydrous benzonitrile ratio of 1:1:200, with 0.125 g of cyclohexanone oxime used, and performed for 7 hours.

The anhydrous benzonitrile shown in FIG. 18 resulted in greater selectivity but lower conversion than the (wet) benzonitrile shown in FIG. 17. Both FIGS. 17 and 18 show high conversion and selectivity in a liquid phase reaction.

Figure 19:
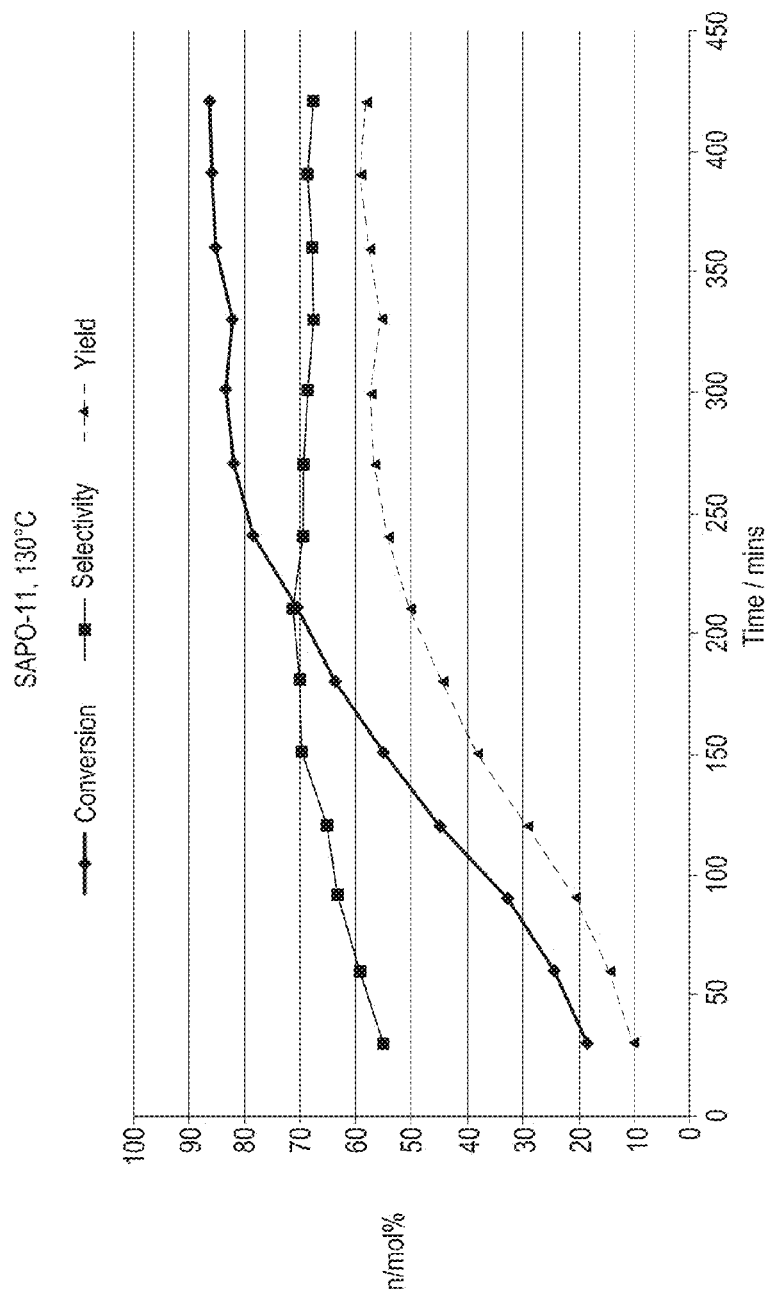

FIG. 19 illustrates a lower conversion and selectivity for a liquid phase reaction with SAPO-11 as the catalyst. The reaction was performed at 130° C., with a catalyst:cyclohexanone oxime:benzonitrile ratio of 1:1:200, with 0.1 g of cyclohexanone oxime used, and run for 7 hours.

Figure 20:
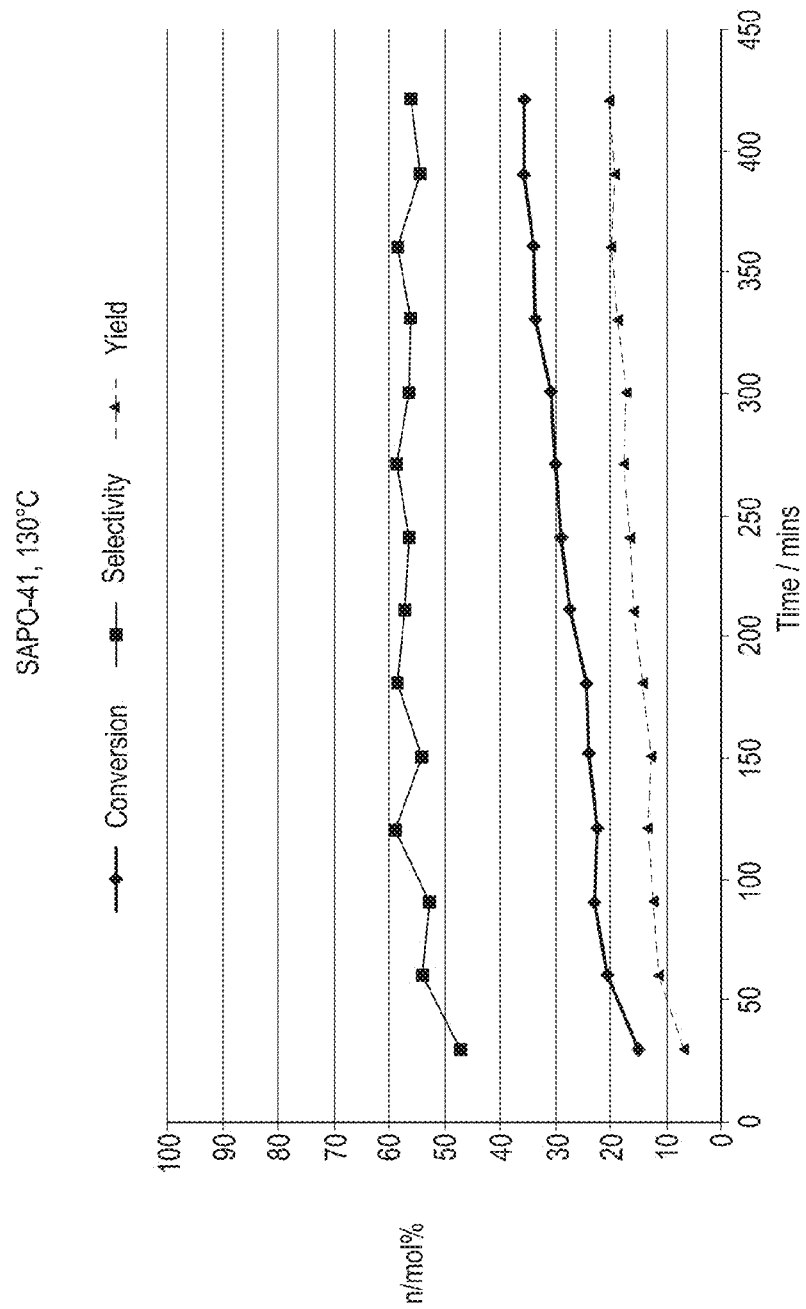

FIG. 20 illustrates an even lower conversion and selectivity for a liquid phase reaction with SAPO-41 as the catalyst. The reaction was performed at 130° C., with a catalyst:cyclohexanone oxime:benzonitrile ratio of 1:1:200, with 0.1 g of cyclohexanone oxime used, and run for 7 hours.

Further liquid test results are provided in Tables 12 and 13. Table 12 presents the conversion, selectivity, and yield for SAPO-37 catalysts with various gel loadings at time intervals during the reaction. Table 13 presents the final conversion and selectivity values taken for each catalyst at the indicated temperature. Benzonitrile was used as the solvent in each of the runs in Tables 12 and 13. SAPO-37(0.21)AN designates the use of anhydrous benzonitrile as the solvent.

TABLE 12

Conversion and selectivity of SAPO-37 catalysts at various temperatures

| System | Temperature ° C. | Time mins | Conversion mol % | Selectivity mol % | Yield mol % |
|---|---|---|---|---|---|
| SAPO-37(0.21) | 130 | 30 | 33.7 | 97.1 | 32.7 |
| SAPO-37(0.21) | 130 | 60 | 55.3 | 95.3 | 52.8 |
| SAPO-37(0.21) | 130 | 90 | 69.5 | 95.0 | 66.0 |
| SAPO-37(0.21) | 130 | 120 | 78.1 | 96.1 | 75.1 |
| SAPO-37(0.21) | 130 | 150 | 84.6 | 95.5 | 80.8 |
| SAPO-37(0.21) | 130 | 180 | 89.3 | 96.0 | 85.7 |
| SAPO-37(0.21) | 130 | 210 | 92.2 | 95.4 | 88.0 |
| SAPO-37(0.21) | 130 | 240 | 94.2 | 95.7 | 90.2 |
| SAPO-37(0.21) | 130 | 270 | 95.6 | 96.7 | 92.4 |
| SAPO-37(0.21) | 130 | 300 | 96.5 | 96.7 | 93.4 |
| SAPO-37(0.21) | 130 | 330 | 97.8 | 96.1 | 94.0 |
| SAPO-37(0.21) | 130 | 360 | 98.2 | 94.6 | 92.9 |
| SAPO-37(0.21) | 130 | 390 | 98.7 | 94.0 | 92.8 |
| SAPO-37(0.21) | 130 | 420 | 98.9 | 93.5 | 92.4 |
| SAPO-37(0.21)AN | 130 | 30 | 30.2 | 100.0 | 30.2 |
| SAPO-37(0.21)AN | 130 | 60 | 54.1 | 99.1 | 53.6 |
| SAPO-37(0.21)AN | 130 | 90 | 71.0 | 98.6 | 70.0 |
| SAPO-37(0.21)AN | 130 | 120 | 82.5 | 99.0 | 81.6 |
| SAPO-37(0.21)AN | 130 | 150 | 88.4 | 98.3 | 86.9 |
| SAPO-37(0.21)AN | 130 | 180 | 93.4 | 97.8 | 91.3 |
| SAPO-37(0.21)AN | 130 | 210 | 96.5 | 97.9 | 94.4 |
| SAPO-37(0.21)AN | 130 | 240 | 97.9 | 97.8 | 95.7 |
| SAPO-37(0.21)AN | 130 | 270 | 98.4 | 98.1 | 96.5 |
| SAPO-37(0.21)AN | 130 | 300 | 99.0 | 98.4 | 97.4 |
| SAPO-37(0.21)AN | 130 | 330 | 99.3 | 97.7 | 97.0 |
| SAPO-37(0.21)AN | 130 | 360 | 99.5 | 97.8 | 97.3 |
| SAPO-37(0.21)AN | 130 | 390 | 99.7 | 97.9 | 97.6 |
| SAPO-37(0.21)AN | 130 | 420 | 99.8 | 97.8 | 97.6 |
| SAPO-37(0.42) | 130 | 30 | 33.5 | 96.4 | 32.3 |
| SAPO-37(0.42) | 130 | 60 | 53.0 | 98.4 | 52.1 |
| SAPO-37(0.42) | 130 | 90 | 69.0 | 94.9 | 65.5 |
| SAPO-37(0.42) | 130 | 120 | 78.3 | 95.7 | 74.9 |
| SAPO-37(0.42) | 130 | 150 | 85.0 | 93.5 | 79.5 |
| SAPO-37(0.42) | 130 | 180 | 89.8 | 93.3 | 83.8 |
| SAPO-37(0.42) | 130 | 210 | 92.3 | 92.7 | 85.5 |
| SAPO-37(0.42) | 130 | 240 | 94.3 | 91.3 | 86.1 |
| SAPO-37(0.42) | 130 | 270 | 96.0 | 90.5 | 86.8 |
| SAPO-37(0.42) | 130 | 300 | 97.1 | 91.1 | 88.5 |
| SAPO-37(0.42) | 130 | 330 | 97.6 | 90.7 | 88.5 |
| SAPO-37(0.42) | 130 | 360 | 98.1 | 91.0 | 89.2 |
| SAPO-37(0.42) | 130 | 390 | 98.5 | 90.7 | 89.3 |
| SAPO-37(0.42) | 130 | 420 | 98.8 | 90.3 | 89.1 |
| SAPO-37(0.63) | 130 | 30 | 38.2 | 91.6 | 35.0 |
| SAPO-37(0.63) | 130 | 60 | 58.4 | 91.5 | 53.4 |
| SAPO-37(0.63) | 130 | 90 | 73.1 | 90.3 | 66.1 |
| SAPO-37(0.63) | 130 | 120 | 80.8 | 90.4 | 73.0 |
| SAPO-37(0.63) | 130 | 150 | 87.0 | 90.9 | 79.1 |
| SAPO-37(0.63) | 130 | 180 | 91.4 | 90.9 | 83.0 |
| SAPO-37(0.63) | 130 | 210 | 94.3 | 90.9 | 85.7 |
| SAPO-37(0.63) | 130 | 240 | 96.5 | 89.3 | 86.2 |
| SAPO-37(0.63) | 130 | 270 | 97.8 | 89.3 | 87.3 |
| SAPO-37(0.63) | 130 | 300 | 98.6 | 88.9 | 87.7 |
| SAPO-37(0.63) | 130 | 330 | 99.3 | 89.9 | 89.2 |
| SAPO-37(0.63) | 130 | 360 | 99.5 | 88.1 | 87.7 |
| SAPO-37(0.63) | 130 | 390 | 99.7 | 88.8 | 88.5 |
| SAPO-37(0.63) | 130 | 420 | 99.8 | 88.4 | 88.2 |
| SAPO-37(0.21) | 150 | 15 | 44.5 | 94.5 | 42.1 |
| SAPO-37(0.21) | 150 | 30 | 75.4 | 95.7 | 72.1 |
| SAPO-37(0.21) | 150 | 45 | 87.3 | 94.7 | 82.7 |
| SAPO-37(0.21) | 150 | 60 | 95.0 | 92.8 | 88.2 |
| SAPO-37(0.21) | 150 | 75 | 97.2 | 92.5 | 89.9 |
| SAPO-37(0.21) | 150 | 90 | 98.7 | 93.7 | 92.4 |
| SAPO-37(0.21) | 150 | 105 | 99.4 | 92.7 | 92.2 |
| SAPO-37(0.21) | 150 | 120 | 99.7 | 91.1 | 90.8 |
| SAPO-37(0.21) | 150 | 135 | 99.8 | 92.5 | 92.3 |
| SAPO-37(0.21) | 150 | 150 | 99.9 | 92.7 | 92.6 |
| SAPO-37(0.21) | 150 | 165 | 99.9 | 91.6 | 91.6 |
| SAPO-37(0.21) | 150 | 180 | 99.9 | 91.4 | 91.4 |
| SAPO-37(0.21) | 150 | 195 | 100.0 | 91.3 | 91.3 |
| SAPO-37(0.21) | 150 | 210 | 100.0 | 91.3 | 91.3 |
| SAPO-37(0.21) | 150 | 225 | 100.0 | 91.0 | 91.0 |
| SAPO-37(0.21) | 150 | 240 | 100.0 | 90.8 | 90.8 |
| SAPO-37(0.42) | 150 | 15 | 44.6 | 94.6 | 42.2 |
| SAPO-37(0.42) | 150 | 30 | 69.8 | 90.2 | 62.9 |
| SAPO-37(0.42) | 150 | 45 | 80.8 | 88.9 | 71.8 |
| SAPO-37(0.42) | 150 | 60 | 87.3 | 89.5 | 78.1 |
| SAPO-37(0.42) | 150 | 75 | 93.2 | 90.4 | 84.2 |
| SAPO-37(0.42) | 150 | 90 | 95.2 | 91.1 | 86.7 |
| SAPO-37(0.42) | 150 | 105 | 96.6 | 90.1 | 87.1 |
| SAPO-37(0.42) | 150 | 120 | 97.9 | 88.0 | 86.1 |
| SAPO-37(0.42) | 150 | 135 | 98.5 | 89.4 | 88.1 |
| SAPO-37(0.42) | 150 | 150 | 99.0 | 89.5 | 88.7 |
| SAPO-37(0.42) | 150 | 165 | 99.3 | 90.6 | 90.0 |
| SAPO-37(0.42) | 150 | 180 | 99.5 | 90.9 | 90.5 |
| SAPO-37(0.42) | 150 | 195 | 99.7 | 91.1 | 90.8 |
| SAPO-37(0.42) | 150 | 210 | 99.8 | 91.0 | 90.8 |
| SAPO-37(0.42) | 150 | 225 | 99.9 | 88.5 | 88.4 |
| SAPO-37(0.42) | 150 | 240 | 99.9 | 88.7 | 88.7 |
| SAPO-37(0.63) | 150 | 15 | 45.5 | 84.3 | 38.3 |
| SAPO-37(0.63) | 150 | 30 | 66.7 | 82.1 | 54.8 |
| SAPO-37(0.63) | 150 | 45 | 79.5 | 84.4 | 67.1 |
| SAPO-37(0.63) | 150 | 60 | 86.7 | 83.3 | 72.2 |
| SAPO-37(0.63) | 150 | 75 | 90.4 | 84.1 | 76.0 |
| SAPO-37(0.63) | 150 | 90 | 92.1 | 85.0 | 78.3 |
| SAPO-37(0.63) | 150 | 105 | 94.7 | 84.1 | 79.6 |
| SAPO-37(0.63) | 150 | 120 | 96.2 | 84.2 | 81.0 |
| SAPO-37(0.63) | 150 | 135 | 97.2 | 84.2 | 81.8 |
| SAPO-37(0.63) | 150 | 150 | 98.0 | 85.2 | 83.5 |
| SAPO-37(0.63) | 150 | 165 | 98.6 | 85.0 | 83.8 |
| SAPO-37(0.63) | 150 | 180 | 98.9 | 85.2 | 84.2 |
| SAPO-37(0.63) | 150 | 195 | 99.2 | 84.3 | 83.6 |
| SAPO-37(0.63) | 150 | 210 | 99.4 | 83.8 | 83.4 |
| SAPO-37(0.63) | 150 | 225 | 99.6 | 83.7 | 83.3 |

TABLE 12-continued

Conversion and selectivity of SAPO-37 catalysts at various temperatures

| System | Temperature ° C. | Time mins | Conversion mol % | Selectivity mol % | Yield mol % |
|---|---|---|---|---|---|
| SAPO-37(0.63) | 150 | 240 | 99.7 | 84.1 | 83.8 |
| SAPO-37(0.21) | 170 | 5 | 27.2 | 97.1 | 26.4 |
| SAPO-37(0.21) | 170 | 10 | 57.9 | 92.7 | 53.7 |
| SAPO-37(0.21) | 170 | 15 | 77.5 | 91.1 | 70.6 |
| SAPO-37(0.21) | 170 | 20 | 88.2 | 91.3 | 80.5 |
| SAPO-37(0.21) | 170 | 25 | 93.9 | 91.2 | 85.6 |
| SAPO-37(0.21) | 170 | 30 | 96.3 | 90.3 | 87.0 |
| SAPO-37(0.21) | 170 | 35 | 97.9 | 91.0 | 89.1 |
| SAPO-37(0.21) | 170 | 40 | 98.6 | 90.4 | 89.2 |
| SAPO-37(0.21) | 170 | 45 | 99.1 | 89.7 | 88.9 |
| SAPO-37(0.21) | 170 | 50 | 99.5 | 91.1 | 90.6 |
| SAPO-37(0.21) | 170 | 55 | 99.7 | 89.9 | 89.6 |
| SAPO-37(0.21) | 170 | 60 | 99.8 | 90.1 | 89.9 |
| SAPO-37(0.42) | 170 | 5 | 18.2 | 96.7 | 17.6 |
| SAPO-37(0.42) | 170 | 10 | 46.5 | 93.4 | 43.4 |
| SAPO-37(0.42) | 170 | 15 | 63.5 | 94.3 | 59.9 |
| SAPO-37(0.42) | 170 | 20 | 75.0 | 94.9 | 71.2 |
| SAPO-37(0.42) | 170 | 25 | 83.4 | 92.0 | 76.7 |
| SAPO-37(0.42) | 170 | 30 | 89.8 | 92.2 | 82.8 |
| SAPO-37(0.42) | 170 | 35 | 93.2 | 90.2 | 84.1 |
| SAPO-37(0.42) | 170 | 40 | 95.5 | 88.8 | 84.8 |
| SAPO-37(0.42) | 170 | 45 | 97.0 | 89.0 | 86.3 |
| SAPO-37(0.42) | 170 | 50 | 98.4 | 90.1 | 88.7 |
| SAPO-37(0.42) | 170 | 55 | 98.8 | 89.3 | 88.2 |
| SAPO-37(0.42) | 170 | 60 | 98.9 | 89.9 | 88.9 |
| SAPO-37(0.63) | 170 | 5 | 27.8 | 79.2 | 22.0 |
| SAPO-37(0.63) | 170 | 10 | 50.9 | 82.9 | 42.2 |
| SAPO-37(0.63) | 170 | 15 | 68.1 | 83.2 | 56.7 |
| SAPO-37(0.63) | 170 | 20 | 76.6 | 83.7 | 64.2 |
| SAPO-37(0.63) | 170 | 25 | 83.3 | 84.9 | 70.7 |
| SAPO-37(0.63) | 170 | 30 | 88.5 | 82.7 | 73.2 |
| SAPO-37(0.63) | 170 | 35 | 91.8 | 82.7 | 75.9 |
| SAPO-37(0.63) | 170 | 40 | 93.5 | 82.3 | 77.0 |
| SAPO-37(0.63) | 170 | 45 | 94.9 | 82.9 | 78.7 |
| SAPO-37(0.63) | 170 | 50 | 96.1 | 82.5 | 79.3 |
| SAPO-37(0.63) | 170 | 55 | 96.9 | 83.9 | 81.3 |
| SAPO-37(0.63) | 170 | 60 | 97.6 | 83.9 | 81.9 |
| SAPO-37(0.21) | 190 | 5 | 41.3 | 98.1 | 40.6 |
| SAPO-37(0.21) | 190 | 10 | 72.0 | 98.0 | 70.5 |
| SAPO-37(0.21) | 190 | 15 | 86.3 | 96.1 | 82.9 |
| SAPO-37(0.21) | 190 | 20 | 92.9 | 92.4 | 85.9 |
| SAPO-37(0.21) | 190 | 25 | 97.3 | 90.6 | 88.1 |
| SAPO-37(0.21) | 190 | 30 | 98.3 | 91.2 | 89.6 |
| SAPO-37(0.21) | 190 | 35 | 99.1 | 91.7 | 90.9 |
| SAPO-37(0.21) | 190 | 40 | 99.5 | 91.1 | 90.6 |
| SAPO-37(0.21) | 190 | 45 | 99.7 | 92.4 | 92.1 |
| SAPO-37(0.21) | 190 | 50 | 99.8 | 89.6 | 89.4 |
| SAPO-37(0.21) | 190 | 55 | 99.9 | 88.7 | 88.6 |
| SAPO-37(0.21) | 190 | 60 | 99.9 | 89.8 | 89.7 |
| SAPO-37(0.42) | 190 | 5 | 29.5 | 100.0 | 29.5 |
| SAPO-37(0.42) | 190 | 10 | 66.4 | 100.0 | 66.4 |
| SAPO-37(0.42) | 190 | 15 | 87.1 | 95.6 | 83.2 |
| SAPO-37(0.42) | 190 | 20 | 93.7 | 95.2 | 89.2 |
| SAPO-37(0.42) | 190 | 25 | 97.0 | 96.3 | 93.4 |
| SAPO-37(0.42) | 190 | 30 | 98.6 | 96.0 | 94.6 |
| SAPO-37(0.42) | 190 | 35 | 99.3 | 96.6 | 96.0 |
| SAPO-37(0.42) | 190 | 40 | 99.7 | 93.2 | 93.0 |
| SAPO-37(0.42) | 190 | 45 | 99.8 | 93.3 | 93.1 |
| SAPO-37(0.42) | 190 | 50 | 99.9 | 91.8 | 91.8 |
| SAPO-37(0.42) | 190 | 55 | 99.9 | 92.3 | 92.2 |
| SAPO-37(0.42) | 190 | 60 | 100.0 | 90.6 | 90.6 |
| SAPO-37(0.63) | 190 | 5 | 35.9 | 85.5 | 30.7 |
| SAPO-37(0.63) | 190 | 10 | 70.8 | 84.3 | 59.6 |
| SAPO-37(0.63) | 190 | 15 | 87.7 | 80.9 | 70.9 |
| SAPO-37(0.63) | 190 | 20 | 92.2 | 80.8 | 74.5 |
| SAPO-37(0.63) | 190 | 25 | 95.8 | 80.0 | 76.7 |
| SAPO-37(0.63) | 190 | 30 | 97.1 | 81.2 | 78.8 |
| SAPO-37(0.63) | 190 | 35 | 98.0 | 79.7 | 78.2 |
| SAPO-37(0.63) | 190 | 40 | 98.7 | 78.9 | 77.9 |
| SAPO-37(0.63) | 190 | 45 | 99.0 | 78.4 | 77.6 |
| SAPO-37(0.63) | 190 | 50 | 99.3 | 79.2 | 78.7 |
| SAPO-37(0.63) | 190 | 55 | 99.5 | 79.0 | 78.5 |
| SAPO-37(0.63) | 190 | 60 | 99.7 | 79.5 | 79.3 |

TABLE 13

Final conversion and selectivity of SAPO-37 catalysts at various temperatures

| | System | Time mins | Conversion mol % | ε-caprolactam selectivity mol % |
|---|---|---|---|---|
| 130° C. | SAPO-37(0.21) | 420 | 98.9 | 93.5 |
| | SAPO-37(0.21)AN | 420 | 99.8 | 97.8 |
| | SAPO-37(0.42) | 420 | 98.8 | 90.3 |
| | SAPO-37(0.63) | 420 | 99.8 | 88.4 |
| 150° C. | SAPO-37(0.21) | 240 | 100.0 | 90.8 |
| | SAPO-37(0.42) | 240 | 99.9 | 88.7 |
| | SAPO-37(0.63) | 240 | 99.7 | 84.1 |
| 170° C. | SAPO-37(0.21) | 60 | 99.8 | 90.1 |
| | SAPO-37(0.42) | 60 | 98.9 | 89.9 |
| | SAPO-37(0.63) | 60 | 97.6 | 83.9 |
| 190° C. | SAPO-37(0.21) | 60 | 99.9 | 89.8 |
| | SAPO-37(0.42) | 60 | 100.0 | 85.4 |
| | SAPO-37(0.63) | 60 | 99.7 | 79.5 |

The results in Tables 12 and 13 indicate high levels of conversion and selectivity using SAPO-37 as the catalyst and benzonitrile as the solvent in a liquid phase reaction. The data in Tables 12 and 13 show conversion greater than 97.5% within the measured times, while selectivity for ε-caprolactam ranged from about 80% for SAPO-37(0.63) at 190° C. to about 98% for SAPO-37(0.21) at 130° C. in anhydrous benzonitrile.

Generally, the SAPO-37(0.21) provided higher selectivity than the SAPO-37(0.42), which in turn provided higher selectivity than the SAPO-37(0.63), although high selectivity and conversion were seen for all three catalysts. These results are consistent with the higher quantity of acid site suggested by the characterization data in Example 2.

Liquid Beckmann Rearrangement of Cyclododecanone Oxime to ω-Laurolactam

The Beckmann rearrangement is also known to be useful in producing ω-laurolactam from cyclododecanone (see FIG. 1B).

The same experimental procedure as for the liquid reactions with cyclohexanone oxime were performed with cyclododecanone oxime using SAPO-37(0.21) and SAPO-11 catalysts. The reaction was performed at 130° C., with 175 mg of cyclododecanone oxime, 100 mg of catalyst, and 20 ml of benzonitrile. The gas chromatogram retention times were 8.4 minutes for cyclododecanone, 10.6 minutes for cyclododecanone oxime, and 11.8 minutes for ω-laurolactam. The results using SAPO-37 (0.21) are provided in FIG. 19 and Table 14. The results using SAPO-11 are provided in FIG. 20.

TABLE 14

Results of liquid cyclododecanone oxime reaction
SAPO-37(0.21), 190° C.

| Time/<br>minutes | Conversion/<br>mol % | Selectivity/<br>mol % | Yield/<br>mol % |
|---|---|---|---|
| 5 | 83.9 | 99.9 | 83.9 |
| 10 | 99.3 | 99.4 | 98.8 |
| 60 | 100.0 | 99.8 | 99.8 |

Figure 21:
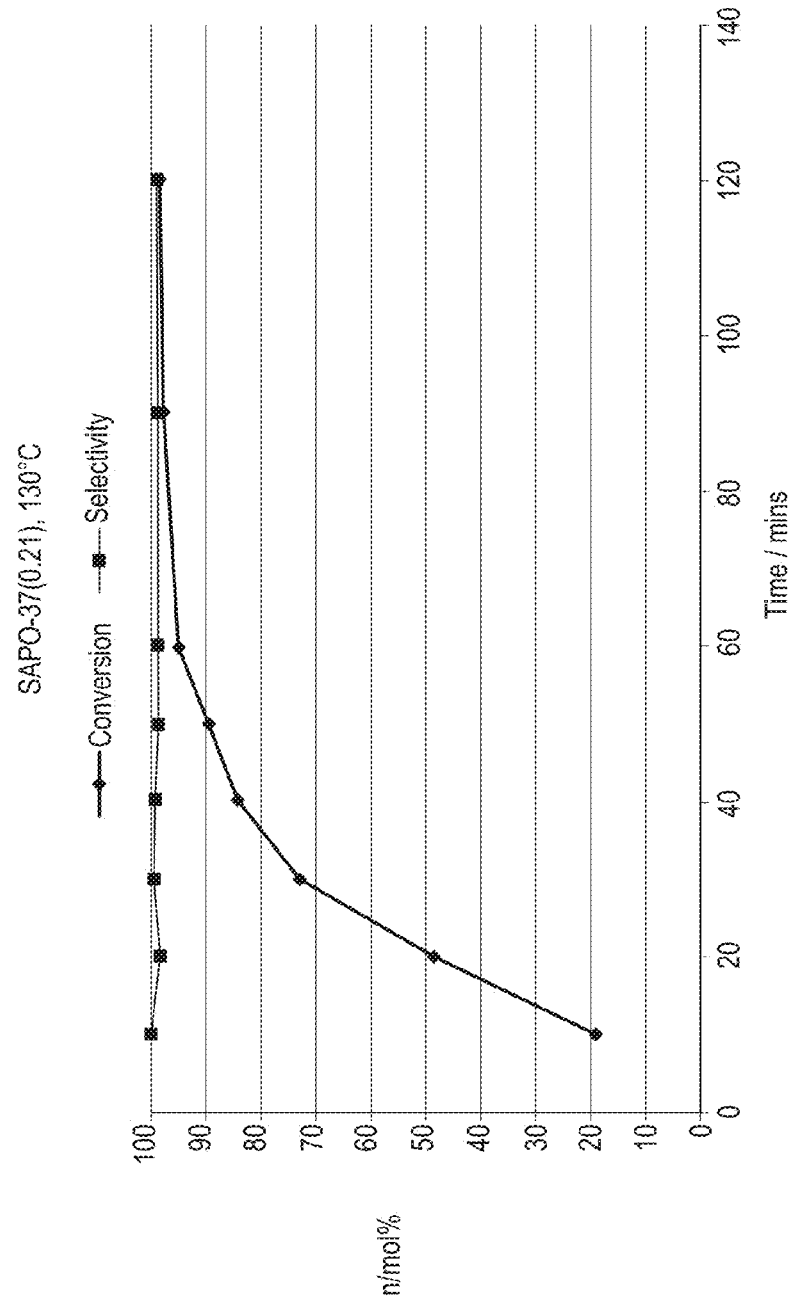
FIGS. 21 and 22 correspond to Example 5, and illustrate the conversion and selectivity results of liquid phase Beckmann rearrangement reactions of cyclododecanone oxime to ω-laurolactam using various catalysts.
Figure 22:
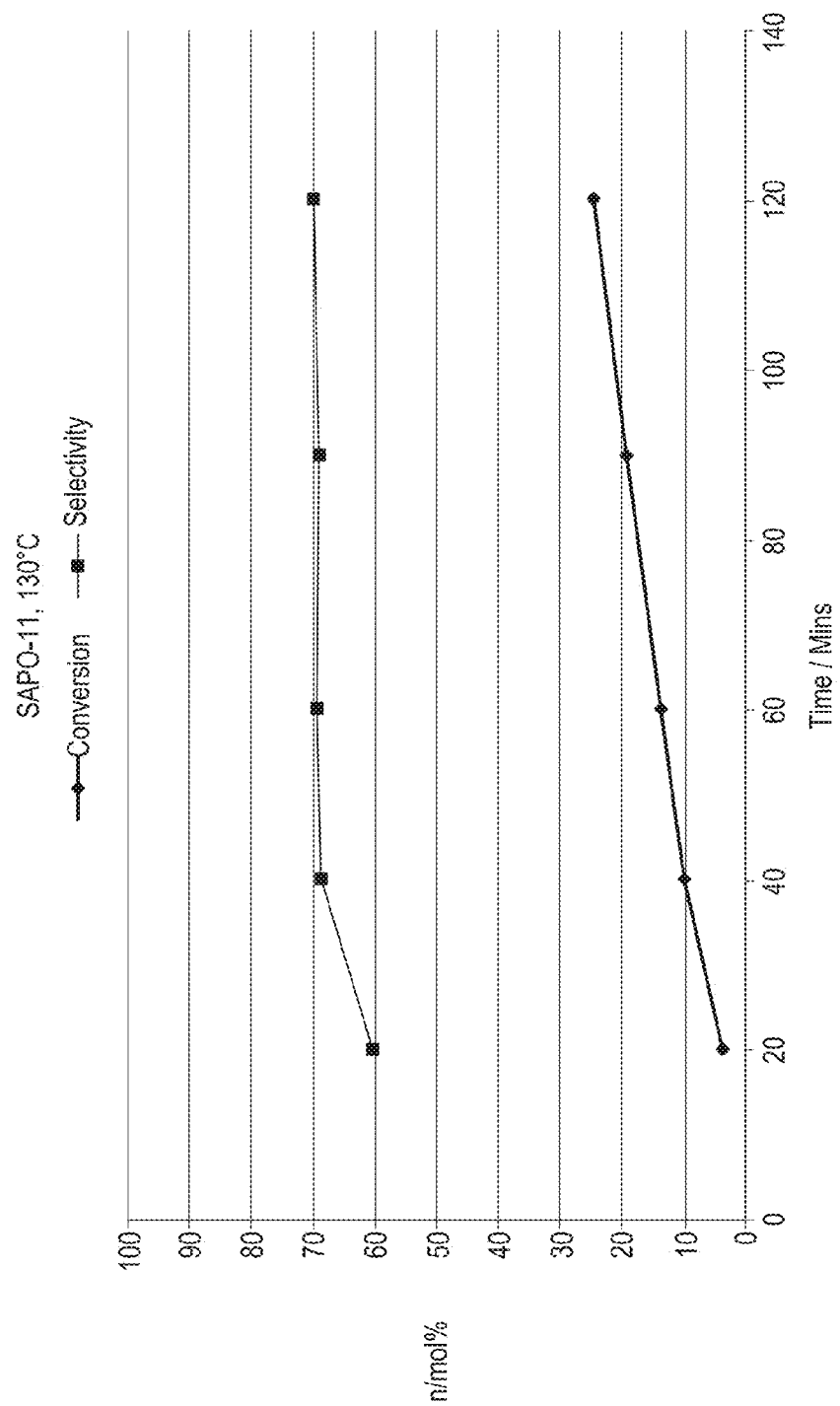

FIG. 21 illustrates very high conversion and selectivity using SAPO-37 as the catalyst, while FIG. 22 illustrates much lower conversion and selectivity using SAPO-37 as the catalyst. The only notably by-product found using SAPO-37 was cyclododecanone.

While the present disclosure is primarily directed to production of ε-caprolactam and ω-laurolactam, it should be understood that the features disclosed herein have application to the production of other lactams and other monomers.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:

1. A method of performing a Beckmann rearrangement reaction comprising the step of:
    reacting an oxime in a liquid phase in the presence of a catalyst to produce a lactam, said catalyst comprising a silicon-containing aluminophosphate with the IZA framework code FAU;
    wherein the oxime is selected from cyclohexanone oxime and cyclododecanone oxime and the lactam is selected from ε-caprolactam and ω-laurolactam.

2. The method of claim 1, wherein the catalyst is a SAPO-37 catalyst.

3. The method of claim 2, wherein the catalyst is prepared from a composition having a gel loading ratio of moles of $SiO_2$ to moles $H_3PO_4$ of from 0.1:1 to 0.8:1.

4. The method of claim 3, wherein the catalyst has a silica weight percentage of from 1 wt. % to 12 wt. % of the total weight of the catalyst.

5. The method of claim 2, wherein the catalyst comprises well-isolated, discrete Brønsted acid sites.

6. The method of claim 5, wherein the catalyst comprises an aluminophosphate framework, the acid sites comprising silicon isomorphously substituted for phosphorous in the framework.

7. The method of claim 1, wherein said reacting step is performed in the presence of a solvent comprising at least one solvent selected from the group consisting of:
    an organic nitrile of the formula $R^1$—CN;
    an aromatic solvent of the formula $R^2$—Ar; and
    an alcohol of the formula $R^3$—OH;
    wherein:
    $R^1$ is $C_1$-$C_8$-alkyl, $C_1$-$C_8$-alkenyl, $C_1$-$C_8$-alkynyl, $C_3$-$C_8$-cycloalkyl; or $C_3$-$C_8$-aralkyl;
    Ar is an aromatic ring and $R^2$ is H, F, Cl, Br; and
    $R^3$ is H, $C_1$-$C_8$-alkyl, $C_1$-$C_8$-alkenyl, $C_1$-$C_8$-alkynyl, $C_3$-$C_8$-cycloalkyl; $C_3$-$C_8$-aralkyl.

8. The method of claim 1, wherein said reacting step is performed at a temperature from 100° C. to 220° C.

9. The method of claim 1 wherein said reacting step further comprises a conversion of the oxime of from 90% to 100% and a selectivity of the lactam of from 70% to 100%.

10. A method of performing a Beckmann rearrangement reaction comprising the step of:
    reacting an oxime in a gas phase in the presence of a catalyst to produce a lactam, said catalyst comprising a silicon-containing aluminophosphates with the IZA framework code FAU;
    wherein said reacting step further comprises the combination of conversion of oxime and selectivity of the lactam is selected from the group consisting of:
        the conversion of the oxime is at least 50% and the selectivity of the lactam is at least 90%; and
        the conversion of the oxime is at least 90% and the selectivity of the lactam is at least 80%;
    wherein the oxime is selected from cyclohexanone oxime and cyclododecanone oxime and the lactam is selected from ε-caprolactam and ω-laurolactam.

11. The method of claim 10, wherein said reacting step further comprises a conversion of the oxime of from 90% to 100% and a selectivity of the lactam of from 90% to 100%.

12. The method of claim 10, wherein said reacting step is performed in the absence of water.

13. The method of claim 10, wherein the catalyst is a SAPO-37 catalyst.

14. The method of claim 13, wherein said reacting step further comprises said SAPO-37 catalyst being prepared from a composition having a gel loading ratio of moles of $SiO_2$ to moles $H_3PO_4$ of from 0.1:1 to 0.8:1.

15. The method of claim 13, wherein said reacting step further comprises said SAPO-37 having a silica weight percentage of from 2 wt. % to 9.1 wt. % of the weight of total weight of the catalyst.

16. The method of claim 13, wherein the catalyst comprises well isolated, discrete Brønsted acid sites.

17. The method of claim 16, wherein the catalyst comprises an aluminophosphate framework, the acid sites comprising silicon isomorphously substituted for phosphorous in the framework.

18. The method of claim 10, wherein said reacting step is performed in the presence of a solvent comprising at least one solvent selected from the group consisting of:
    an organic nitrile of the formula $R^1$—CN;
    an aromatic solvent of the formula $R^2$—Ar; and
    an alcohol of the formula $R^3$—OH;
    wherein
    $R^1$ is $C_1$-$C_8$-alkyl, $C_1$-$C_8$-alkenyl, $C_1$-$C_8$-alkynyl, $C_3$-$C_8$-cycloalkyl; or $C_3$-$C_8$ aralkyl;
    Ar is an aromatic ring and $R^2$ is H, F, Cl, Br; and
    $R^3$ is H, $C_1$-$C_8$-alkyl, $C_1$-$C_8$-alkenyl, $C_1$-$C_8$-alkynyl, $C_3$-$C_8$-cycloalkyl; $C_3$-$C_8$-aralkyl.

19. The method of claim 1, wherein the oxime is cyclohexanone oxime and the lactam is ε-caprolactam.

20. The method of claim 1, wherein the oxime is cyclododecanone oxime and the lactam is ω-laurolactam.

21. The method of claim 10, wherein the oxime is cyclohexanone oxime and the lactam is ε-caprolactam.

22. The method of claim 10, wherein the oxime is cyclododecanone oxime and the lactam is ω-laurolactam.

* * * * *